United States Patent
Fazio et al.

(10) Patent No.: US 9,775,636 B2
(45) Date of Patent: Oct. 3, 2017

(54) DEVICES, SYSTEMS, AND METHODS FOR TREATING HEART FAILURE

(71) Applicant: DC Devices, Inc., Tewksbury, MA (US)

(72) Inventors: George Fazio, Weston, MA (US); Matthew Finch, Somerville, MA (US); John Mitzel, Chester, NH (US)

(73) Assignee: Corvia Medical, Inc., Tewksbury, MA (US)

( * ) Notice: Subject to any disclaimer, the term of this patent is extended or adjusted under 35 U.S.C. 154(b) by 205 days.

(21) Appl. No.: 14/205,365

(22) Filed: Mar. 11, 2014

(65) Prior Publication Data

US 2014/0277045 A1    Sep. 18, 2014

Related U.S. Application Data

(60) Provisional application No. 61/778,382, filed on Mar. 12, 2013.

(51) Int. Cl.
*A61B 17/32* (2006.01)
*A61B 17/3205* (2006.01)
(Continued)

(52) U.S. Cl.
CPC ............... *A61B 17/320016* (2013.01); *A61B 17/32053* (2013.01); *A61B 17/320725* (2013.01);
(Continued)

(58) Field of Classification Search
CPC ...... A61B 17/320016; A61B 17/32053; A61B 2017/3488; A61B 2017/320064;
(Continued)

(56) References Cited

U.S. PATENT DOCUMENTS 4,018,228 A    4/1977    Goosen
4,705,507 A    11/1987   Boyles
(Continued)

FOREIGN PATENT DOCUMENTS

EP    1470785    10/2004
EP    2537490    12/2012
(Continued)

OTHER PUBLICATIONS

Ad et al., "A one way valved atrial septal patch: A new surgical technique and its clinical application", The Journal of Thoracic and Cardiovascular Surgery, vol. 111, Apr. 1996, pp. 841-848.
(Continued)

*Primary Examiner* — Richard Louis
(74) *Attorney, Agent, or Firm* — Helen S. Liu

(57) ABSTRACT

The present teachings provide devices and methods for percutaneously removing internal tissue. Specifically, one aspect of the present teachings provides a tissue incising element with a sharp cutting edge and a longitudinal lumen and a tissue stabilizer slidably disposed within the longitudinal lumen of the tissue incising element. The tissue incising element has a deployed configuration during tissue cutting and a small collapsed configuration during the percutaneous delivery and removal. The tissue stabilizer includes a tissue supporting/gripping element configured to support tissue during incising and capture the removed tissue.

15 Claims, 12 Drawing Sheets

(51) Int. Cl.
*A61B 17/3207* (2006.01)
*A61B 17/00* (2006.01)
*A61B 17/22* (2006.01)
*A61B 17/34* (2006.01)

(52) U.S. Cl.
CPC ............... *A61B 2017/00247* (2013.01); *A61B 2017/22061* (2013.01); *A61B 2017/320064* (2013.01); *A61B 2017/3488* (2013.01)

(58) Field of Classification Search
CPC .. A61B 2017/22061; A61B 17/320725; A61B 2017/00247
See application file for complete search history.

(56) References Cited

U.S. PATENT DOCUMENTS

| | | | |
|---|---|---|---|
| 5,100,423 A * | 3/1992 | Fearnot | 606/159 |
| 5,108,420 A | 4/1992 | Marks | |
| 5,171,233 A | 12/1992 | Amplatz et al. | |
| 5,334,217 A | 8/1994 | Das | |
| 5,429,144 A | 7/1995 | Wilk | |
| 5,556,408 A * | 9/1996 | Farhat | 606/180 |
| 5,578,045 A | 11/1996 | Das | |
| 5,693,090 A | 12/1997 | Unsworth et al. | |
| 5,702,412 A | 12/1997 | Popov et al. | |
| 5,725,552 A | 3/1998 | Kotula et al. | |
| 5,824,071 A | 10/1998 | Nelson et al. | |
| 5,876,436 A | 3/1999 | Vanney et al. | |
| 6,050,936 A | 4/2000 | Schweich et al. | |
| 6,077,281 A | 6/2000 | Das | |
| 6,123,715 A | 9/2000 | Amplatz | |
| 6,156,055 A | 12/2000 | Ravenscroft | |
| 6,190,353 B1 | 2/2001 | Makower et al. | |
| 6,193,734 B1 | 2/2001 | Bolduc et al. | |
| 6,258,119 B1 | 7/2001 | Hussein et al. | |
| 6,334,864 B1 | 1/2002 | Amplatz et al. | |
| 6,350,277 B1 | 2/2002 | Kocur | |
| 6,355,052 B1 | 3/2002 | Neuss et al. | |
| 6,355,056 B1 | 3/2002 | Pinheiro | |
| 6,383,195 B1 | 5/2002 | Richard | |
| 6,395,017 B1 | 5/2002 | Dwyer et al. | |
| 6,402,777 B1 | 6/2002 | Globerman et al. | |
| 6,409,716 B1 | 6/2002 | Sahatjian et al. | |
| 6,440,152 B1 | 8/2002 | Gainor et al. | |
| 6,454,795 B1 | 9/2002 | Chuter | |
| 6,458,153 B1 | 10/2002 | Bailey et al. | |
| 6,468,303 B1 | 10/2002 | Amplatz et al. | |
| 6,527,746 B1 | 3/2003 | Oslund et al. | |
| 6,626,936 B2 | 9/2003 | Stinson | |
| 6,641,610 B2 | 11/2003 | Wolf et al. | |
| 6,645,143 B2 | 11/2003 | Van Tassel et al. | |
| 6,666,885 B2 | 12/2003 | Moe | |
| 6,712,836 B1 | 3/2004 | Berg et al. | |
| 6,837,901 B2 | 1/2005 | Rabkin et al. | |
| 6,866,679 B2 | 3/2005 | Kusleika | |
| 6,911,037 B2 | 6/2005 | Gainor et al. | |
| 6,913,614 B2 | 7/2005 | Marino et al. | |
| 6,936,058 B2 | 8/2005 | Forde et al. | |
| 6,979,343 B2 | 12/2005 | Russo et al. | |
| 7,001,409 B2 | 2/2006 | Amplatz et al. | |
| 7,097,653 B2 | 8/2006 | Freudenthal et al. | |
| 7,105,024 B2 | 9/2006 | Richelsoph | |
| 7,159,593 B2 | 1/2007 | McCarthy et al. | |
| 7,226,466 B2 | 6/2007 | Opolski | |
| 7,317,951 B2 | 1/2008 | Schneider et al. | |
| 7,338,514 B2 | 3/2008 | Wahr et al. | |
| 7,419,498 B2 | 9/2008 | Opolski et al. | |
| 7,445,630 B2 | 11/2008 | Lashinski et al. | |
| 7,473,266 B2 | 1/2009 | Glaser | |
| 7,485,141 B2 | 2/2009 | Majercak et al. | |
| 7,524,330 B2 | 4/2009 | Berreklouw | |
| 7,530,995 B2 | 5/2009 | Quijano et al. | |
| 7,625,392 B2 | 12/2009 | Coleman et al. | |
| 7,658,747 B2 | 2/2010 | Forde et al. | |
| 7,699,297 B2 | 4/2010 | Cicenas et al. | |
| 7,766,966 B2 | 8/2010 | Richelsoph | |
| 7,819,890 B2 | 10/2010 | Russo et al. | |
| 7,842,026 B2 | 11/2010 | Cahill et al. | |
| 7,871,419 B2 | 1/2011 | Devellian et al. | |
| 7,927,370 B2 | 4/2011 | Webler et al. | |
| 7,976,564 B2 | 7/2011 | Blaeser et al. | |
| 8,034,061 B2 | 10/2011 | Amplatz et al. | |
| 8,043,360 B2 | 10/2011 | McNamara et al. | |
| 8,048,147 B2 | 11/2011 | Adams | |
| 8,070,708 B2 | 12/2011 | Rottenberg et al. | |
| 8,091,556 B2 | 1/2012 | Keren et al. | |
| 8,157,860 B2 | 4/2012 | McNamara et al. | |
| 8,172,896 B2 | 5/2012 | McNamara et al. | |
| 8,252,042 B2 | 8/2012 | McNamara et al. | |
| 8,460,372 B2 | 6/2013 | McNamara et al. | |
| 2001/0029368 A1 | 10/2001 | Berube | |
| 2002/0029061 A1 | 3/2002 | Amplatz et al. | |
| 2002/0062135 A1 | 5/2002 | Mazzocchi et al. | |
| 2002/0072765 A1 | 6/2002 | Mazzocchi et al. | |
| 2002/0077698 A1 | 6/2002 | Peredo | |
| 2002/0082525 A1 | 6/2002 | Oslund et al. | |
| 2002/0082613 A1 | 6/2002 | Hathaway et al. | |
| 2002/0095172 A1 | 7/2002 | Mazzocchi et al. | |
| 2002/0095173 A1 | 7/2002 | Mazzocchi et al. | |
| 2002/0143289 A1 | 10/2002 | Ellis et al. | |
| 2002/0161424 A1 | 10/2002 | Rapacki et al. | |
| 2002/0161432 A1 | 10/2002 | Mazzucco et al. | |
| 2002/0165606 A1 | 11/2002 | Wolf et al. | |
| 2002/0169377 A1 | 11/2002 | Khairkhahan et al. | |
| 2002/0173742 A1 | 11/2002 | Keren et al. | |
| 2002/0177894 A1 | 11/2002 | Acosta et al. | |
| 2002/0183826 A1 | 12/2002 | Dorn et al. | |
| 2002/0198563 A1 | 12/2002 | Gainor et al. | |
| 2004/0044351 A1 | 3/2004 | Searle | |
| 2004/0087937 A1 | 5/2004 | Eggers et al. | |
| 2004/0093075 A1 | 5/2004 | Kuehne | |
| 2004/0102719 A1 | 5/2004 | Keith et al. | |
| 2004/0111095 A1 | 6/2004 | Gordon et al. | |
| 2004/0133236 A1 | 7/2004 | Chanduszko et al. | |
| 2004/0143292 A1 | 7/2004 | Marino | |
| 2004/0162514 A1 | 8/2004 | Alferness et al. | |
| 2004/0176788 A1 | 9/2004 | Opolski | |
| 2004/0193261 A1 | 9/2004 | Berreklouw | |
| 2004/0206363 A1 | 10/2004 | McCarthy et al. | |
| 2004/0220653 A1 | 11/2004 | Borg et al. | |
| 2004/0236308 A1 | 11/2004 | Herweck et al. | |
| 2004/0243143 A1 | 12/2004 | Corcoran et al. | |
| 2004/0267306 A1 | 12/2004 | Blaeser et al. | |
| 2005/0049692 A1 | 3/2005 | Numamoto et al. | |
| 2005/0065548 A1 | 3/2005 | Marino et al. | |
| 2005/0065589 A1 | 3/2005 | Schneider et al. | |
| 2005/0070934 A1 | 3/2005 | Tanaka et al. | |
| 2005/0075655 A1 | 4/2005 | Bumbalough et al. | |
| 2005/0075665 A1 * | 4/2005 | Brenzel | A61B 17/0057 606/213 |
| 2005/0080400 A1 | 4/2005 | Corcoran et al. | |
| 2005/0080430 A1 * | 4/2005 | Wright, Jr. | A61B 17/22031 606/108 |
| 2005/0148925 A1 | 7/2005 | Rottenberg et al. | |
| 2005/0165344 A1 | 7/2005 | Dobak | |
| 2005/0187616 A1 | 8/2005 | Realyvasquez | |
| 2005/0240205 A1 | 10/2005 | Berg et al. | |
| 2005/0267523 A1 | 12/2005 | Devellian et al. | |
| 2005/0273075 A1 | 12/2005 | Krulevitch et al. | |
| 2005/0288722 A1 | 12/2005 | Eigler et al. | |
| 2006/0004434 A1 | 1/2006 | Forde et al. | |
| 2006/0009715 A1 | 1/2006 | Khairkhahan et al. | |
| 2006/0009800 A1 | 1/2006 | Christianson et al. | |
| 2006/0122646 A1 | 6/2006 | Corcoran et al. | |
| 2006/0122647 A1 | 6/2006 | Callaghan et al. | |
| 2006/0136043 A1 | 6/2006 | Cully et al. | |
| 2006/0155305 A1 | 7/2006 | Freudenthal et al. | |
| 2006/0184088 A1 | 8/2006 | Van Bibber et al. | |
| 2006/0241745 A1 | 10/2006 | Solem | |
| 2006/0247680 A1 | 11/2006 | Amplatz et al. | |
| 2006/0253184 A1 | 11/2006 | Amplatz | |
| 2006/0276882 A1 | 12/2006 | Case et al. | |
| 2007/0016250 A1 | 1/2007 | Blaeser et al. | |

(56) References Cited

U.S. PATENT DOCUMENTS

| | | |
|---|---|---|
| 2007/0027528 A1 | 2/2007 | Agnew |
| 2007/0038295 A1 | 2/2007 | Case et al. |
| 2007/0043431 A1 | 2/2007 | Melsheimer |
| 2007/0088388 A1 | 4/2007 | Opolski et al. |
| 2007/0118207 A1 | 5/2007 | Amplatz et al. |
| 2007/0123934 A1 | 5/2007 | Whisenant et al. |
| 2007/0168019 A1 | 7/2007 | Amplatz et al. |
| 2007/0185513 A1 | 8/2007 | Woolfson et al. |
| 2007/0209957 A1 | 9/2007 | Glenn et al. |
| 2007/0225759 A1 | 9/2007 | Thommen et al. |
| 2007/0265658 A1 | 11/2007 | Nelson et al. |
| 2007/0270741 A1 | 11/2007 | Hassett et al. |
| 2007/0282157 A1 | 12/2007 | Rottenberg et al. |
| 2008/0015619 A1 | 1/2008 | Figulla et al. |
| 2008/0033425 A1 | 2/2008 | Davis et al. |
| 2008/0033543 A1 | 2/2008 | Gurskis et al. |
| 2008/0039804 A1 | 2/2008 | Edmiston et al. |
| 2008/0039881 A1* | 2/2008 | Greenberg ............ A61B 17/22 606/170 |
| 2008/0039922 A1 | 2/2008 | Miles et al. |
| 2008/0058940 A1 | 3/2008 | Wu et al. |
| 2008/0071135 A1 | 3/2008 | Shaknovich |
| 2008/0086168 A1 | 4/2008 | Cahill |
| 2008/0103508 A1 | 5/2008 | Karakurum |
| 2008/0119891 A1 | 5/2008 | Miles et al. |
| 2008/0125861 A1 | 5/2008 | Webler et al. |
| 2008/0154302 A1 | 6/2008 | Opolski et al. |
| 2008/0154351 A1 | 6/2008 | Leewood et al. |
| 2008/0172123 A1 | 7/2008 | Yadin |
| 2008/0183279 A1 | 7/2008 | Bailey et al. |
| 2008/0188880 A1* | 8/2008 | Fischer .......... A61B 17/320016 606/170 |
| 2008/0188888 A1 | 8/2008 | Adams et al. |
| 2008/0215008 A1 | 9/2008 | Nance et al. |
| 2008/0228264 A1 | 9/2008 | Li et al. |
| 2008/0249612 A1 | 10/2008 | Osborne et al. |
| 2008/0262592 A1 | 10/2008 | Jordan et al. |
| 2008/0312679 A1 | 12/2008 | Hardert et al. |
| 2009/0018562 A1 | 1/2009 | Amplatz et al. |
| 2009/0025820 A1 | 1/2009 | Adams |
| 2009/0030495 A1 | 1/2009 | Koch |
| 2009/0054805 A1* | 2/2009 | Boyle, Jr. .......... A61B 10/0266 600/564 |
| 2009/0062841 A1 | 3/2009 | Amplatz et al. |
| 2009/0082803 A1 | 3/2009 | Adams et al. |
| 2009/0099647 A1 | 4/2009 | Glimsdale et al. |
| 2009/0112050 A1 | 4/2009 | Farnan et al. |
| 2009/0112244 A1 | 4/2009 | Freudenthal et al. |
| 2009/0131978 A1 | 5/2009 | Gainor et al. |
| 2009/0171386 A1 | 7/2009 | Amplatz et al. |
| 2009/0187214 A1 | 7/2009 | Amplatz et al. |
| 2009/0209855 A1 | 8/2009 | Drilling et al. |
| 2009/0210047 A1 | 8/2009 | Amplatz et al. |
| 2009/0210048 A1 | 8/2009 | Amplatz et al. |
| 2009/0234443 A1 | 9/2009 | Ottma et al. |
| 2009/0264991 A1 | 10/2009 | Paul et al. |
| 2009/0270840 A1 | 10/2009 | Miles et al. |
| 2009/0270909 A1 | 10/2009 | Oslund et al. |
| 2010/0022940 A1 | 1/2010 | Thompson |
| 2010/0023046 A1 | 1/2010 | Heidner et al. |
| 2010/0023048 A1 | 1/2010 | Mach |
| 2010/0023121 A1 | 1/2010 | Evdokimov et al. |
| 2010/0030321 A1 | 2/2010 | Mach |
| 2010/0049307 A1 | 2/2010 | Ren |
| 2010/0057192 A1 | 3/2010 | Celermajer |
| 2010/0063578 A1 | 3/2010 | Ren et al. |
| 2010/0094335 A1 | 4/2010 | Gerberding et al. |
| 2010/0106235 A1 | 4/2010 | Kariniemi et al. |
| 2010/0121370 A1 | 5/2010 | Kariniemi |
| 2010/0131053 A1 | 5/2010 | Agnew |
| 2010/0179491 A1 | 7/2010 | Adams et al. |
| 2010/0211046 A1 | 8/2010 | Adams et al. |
| 2010/0234881 A1 | 9/2010 | Blaeser et al. |
| 2010/0249909 A1 | 9/2010 | McNamara et al. |
| 2010/0249910 A1 | 9/2010 | McNamara et al. |
| 2010/0256548 A1 | 10/2010 | McNamara et al. |
| 2010/0256753 A1 | 10/2010 | McNamara et al. |
| 2010/0298755 A1 | 11/2010 | McNamara et al. |
| 2010/0324588 A1 | 12/2010 | Miles et al. |
| 2011/0004239 A1 | 1/2011 | Russo et al. |
| 2011/0004296 A1 | 1/2011 | Lutter et al. |
| 2011/0022079 A1 | 1/2011 | Miles et al. |
| 2011/0071623 A1 | 3/2011 | Finch et al. |
| 2011/0071624 A1 | 3/2011 | Finch et al. |
| 2011/0093062 A1 | 4/2011 | Cartledge et al. |
| 2011/0106149 A1 | 5/2011 | Ryan et al. |
| 2011/0112633 A1 | 5/2011 | Devellian et al. |
| 2011/0130784 A1 | 6/2011 | Kusleika |
| 2011/0190874 A1 | 8/2011 | Celermajer et al. |
| 2011/0213364 A1 | 9/2011 | Davis et al. |
| 2011/0218477 A1 | 9/2011 | Keren et al. |
| 2011/0218478 A1 | 9/2011 | Keren et al. |
| 2011/0218479 A1 | 9/2011 | Rottenberg et al. |
| 2011/0218480 A1 | 9/2011 | Rottenberg et al. |
| 2011/0218481 A1 | 9/2011 | Rottenberg |
| 2011/0257723 A1 | 10/2011 | McNamara et al. |
| 2011/0283871 A1 | 11/2011 | Adams |
| 2011/0295182 A1 | 12/2011 | Finch et al. |
| 2011/0295183 A1 | 12/2011 | Finch et al. |
| 2011/0295362 A1 | 12/2011 | Finch et al. |
| 2011/0295366 A1 | 12/2011 | Finch et al. |
| 2011/0306916 A1 | 12/2011 | Nitzan et al. |
| 2011/0307000 A1 | 12/2011 | Amplatz et al. |
| 2012/0053686 A1 | 3/2012 | McNamara et al. |
| 2012/0130301 A1 | 5/2012 | McNamara et al. |
| 2012/0165928 A1 | 6/2012 | Nitzan et al. |
| 2012/0259263 A1* | 10/2012 | Celermajer ........ A61B 18/1492 604/8 |
| 2012/0265296 A1 | 10/2012 | McNamara et al. |
| 2012/0289882 A1 | 11/2012 | McNamara et al. |
| 2012/0290062 A1 | 11/2012 | McNamara et al. |
| 2013/0041359 A1* | 2/2013 | Asselin ............ A61B 17/32053 606/27 |
| 2013/0178783 A1 | 7/2013 | McNamara et al. |
| 2013/0178784 A1 | 7/2013 | McNamara et al. |
| 2013/0184633 A1 | 7/2013 | McNamara et al. |
| 2013/0184634 A1 | 7/2013 | McNamara et al. |
| 2013/0204175 A1 | 8/2013 | Sugimoto |
| 2013/0231737 A1 | 9/2013 | McNamara et al. |
| 2013/0267885 A1 | 10/2013 | Celermajer et al. |
| 2013/0281988 A1 | 10/2013 | Magnin |
| 2014/0012181 A1 | 1/2014 | Sugimoto |

FOREIGN PATENT DOCUMENTS

| | | |
|---|---|---|
| WO | 9527448 | 10/1995 |
| WO | 2008058940 | 5/2008 |
| WO | 2010111666 | 9/2010 |
| WO | 2014150106 | 9/2013 |

OTHER PUBLICATIONS

Althoff et al., "Long-Term Follow up of a Fenestrated Amplatzer Atrial Septal Occluder in Pulmonary Arterial Hypertension," Chest 2008, 133:183-85, 5 pages.

Atz et al., "Preoperative Management of Pulmonary Venous Hypertension in Hypoplastic Left Heart Syndrome With Restrictive Atrial Septal Defect", The American Journal of Cardiology, vol. 83, Apr. 15, 1999, pp. 1224-1228.

Bailey, "Nanotechnofogy in Prosthetic Heart Valves," approx. date 2005, presentation, 31 pages.

Bolling, "Direct Flow Medical—My Valve is Better." Apr. 23, 2009, presentation, 21 pages.

Cheatham, John P., "Intervention in the critically ill neonate and infant with hypoplastic left heart syndrome and intact atrial septum", Journal of Interventional Cardiology, vol. 14, No. 3, 2001, pp. 357-366.

Coselli, Joseph S., "No! valve replacement: patient prosthetic mismatch rarely occurs," Texas Heart insitute, Apr. 25, 2009, 75 pages.

(56) References Cited

OTHER PUBLICATIONS

Design News, "Low Power Piezo Motion", http://www.designnews.com/document.asp?doc-id=229053&dfpPParams&dfpPParams=ht-13,aid-229053&dfpLayout=article, May 14, 2010, 3 pages.
European Application Serial No. EP10772411.4, European Search Opinion and Supplementary European Search Report dated Mar. 16, 2012, 5 pages.
European Application Serial No. EP12180631.9, European Search Report dated Nov. 19, 2012, 5 pages.
Gaudiani et al., "A Philosophical Approach to Mitral Valve Repair," Apr. 24, 2009, presentation, 28 pages.
Hijazi, "Valve Implantation, Ziyad M, Hijazi," May 10, 2007, presentation, 36 pages.
International Application Serial No. PCT/AU2007/001704, International Pretiminaty Report on Patentability, dated Aug. 22, 2008, 5 pages.
International Application Serial No. PCT/AU2007/001704, International Search Report, dated Jan. 16, 2008, 4 pages.
International Application Serial No. PCT/AU2007/001704, Written Opinion, dated Jan. 16, 2008, 5 pages.
International Application Serial No. PCT/US2010/026574, International Preliminary Report on Patentability, dated Nov. 10, 2011, 6 pages.
International Application Serial No. PCT/US2010/020574, International Search Report, dated Nov. 19, 2010, 5 pages.
International Application Serial No. PCT/US2010/058110, international Preliminary Report on Patentability, dated Nov. 27, 2012, 7 pages.
International Application Serial No. PCT/US2010/058110, International Search Report and Written Opinion, dated Aug. 26, 2011, 12 pages.
International Application Serial No. PCT/US2011/022895, International Search Report & Written Opinion, dated Oct. 24, 2011, 10 pages.
International Application Serial No. PCT/US2011/041841, International Preliminary Report on Patentability and Written Opinion, dated Jun. 6, 2013, 7 pages.
International Application Serial No. PCT/US2011/041841, International Search Report and Written Opinion, dated Feb. 9, 2012, 10 pages.
International Application Serial No. PCT/US2012/024680, International Preliminary Report on Patentability and Written Opinion, dated Aug. 22, 2013, 6 pages.
International Application Serial No. PCT/US2012/024680, International Search Report and Written Opinion, dated Oct. 23, 2012, 10 pages.
International Application Serial No. PCT/US2012/071588, International Search Report and Written Opinion, dated Apr. 19, 2013, DC Devices, Inc., 17 pages.
Larios et al., "The Use of an Artificial Foraminal Valve Prosthesis in the Closure of Interatrial and Interventricular Septal Defects." Dis. Chest. 1959: 36; 631-41, 11 pages.
Leon, "Transcatheter Aortic Valve Therapy: Summary Thoughts," Jun. 24, 2009, presentation, 19 pages.
Merchant et al., "Advances in Arrhythmia and Electrophysiology: Implantable Sensors for Heart Failure", Circ. Arrhythm, Electrophysiol,, vol. 3, Dec. 2010, pp. 657-667.
Moses, "The Good, the Bad and the Ugly of Transcatheter AVR," Jul. 10, 2009, presentation, 28 pages.
O'Loughlin et al., "Insertion of a Fenestrated Arnpiatzer Atrial Sestosotomy Device for Severe Pulmonary Hypertension," Heart Lung Circ. 2006, 15(4):275-77, 3 pages.
Park et al., "Blade atrial septostomy: collaborative study", Circulation, Journal of the American Heart Association, vol. 66, No. 2, Aug. 1982, pp. 258-266.
Pedra et al., "Stent Implantation to Create Interatrial Communications in Patients With Complex Congenital Heart Disease", Catheterization and Cardiovascular interventions 47, Jan. 27, 1999, pp. 310-313,
Perry et al., "Creation and Maintenance of an Adequate Interatrial Communicationin left Atrioventricular Valve Atresia or Stenosis", The American Journal of Cardiology, vol. 58, Sep. 15, 1986, pp. 622-626.
Philips et al, "Ventriculofemoroatrial shunt: a viable alternative for the treatment of hydrocephalus", J. Neurosurg., vol. 86, Jun. 1997, pp. 1063-1068.
Sommer et al., "Transcatheter Creation of Atrial Septal Defect and Fontan Fenestration with "Butterfly" Stent Technique", Supplement to Journal of the American College of Cardiology, vol. 33, No. 2, Supplement A, Feb. 1999, 3 pages.
Stone, "Transcatheter Devices for Mitral Valve Repair, Surveying the Landscape," Jul. 10, 2009, presentation, 48 pages.
Stormer et at, "Comparative Study of in vitro Flow Characteristics between a Human Aortic Valve and a Designed Aortic Valve and Six Corresponding Types of Prosthetic Heart Valves," Eur. Surg. Res. 6: 117-131 (1976), 15 pages.
Watterson et al., "Very Small Pulmonary Arteries: Central End-to-Side Shunt", Ann. Thorc. Surg., vol. 52, No. 5, Nov. 1991, pp. 1132-1137.

\* cited by examiner

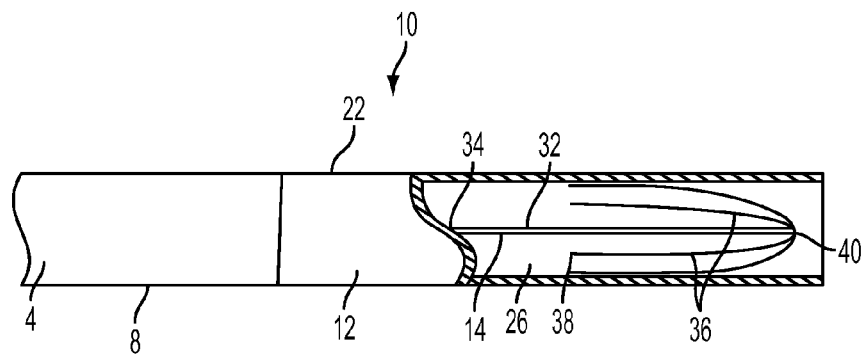
FIG. 2
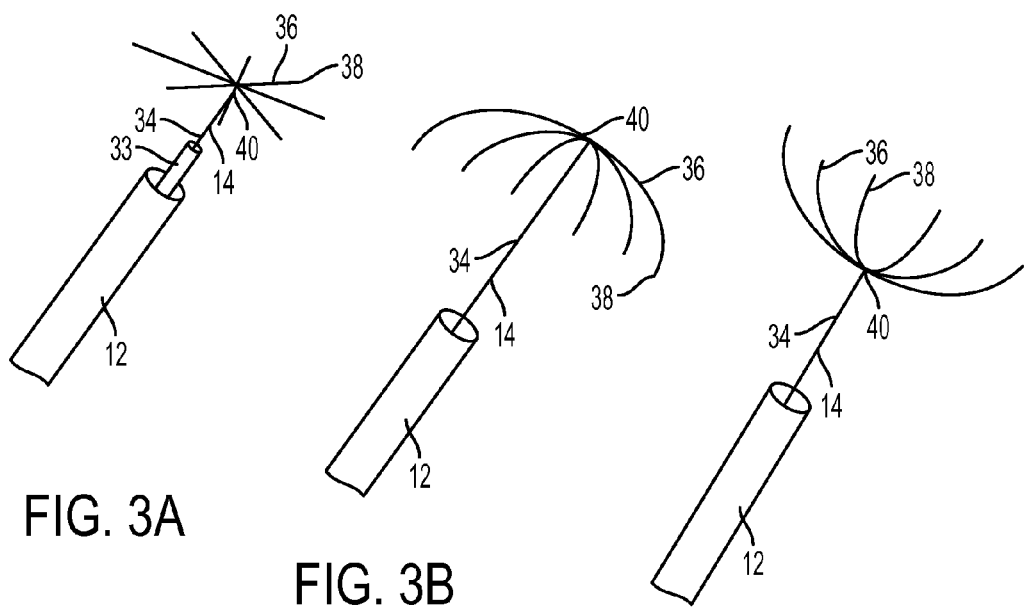
FIG. 3A
FIG. 3B
FIG. 3C

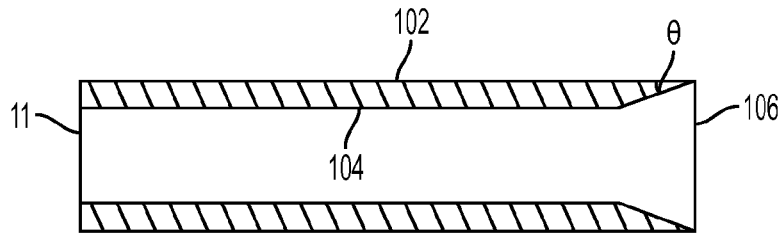
FIG. 13A
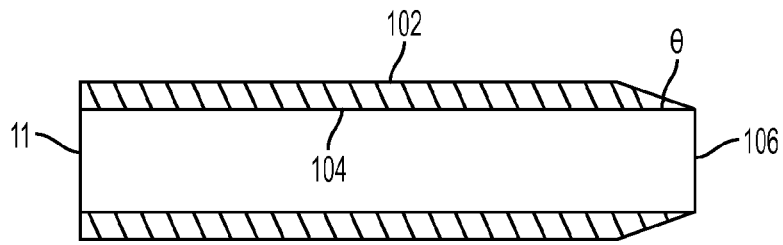
FIG. 13B
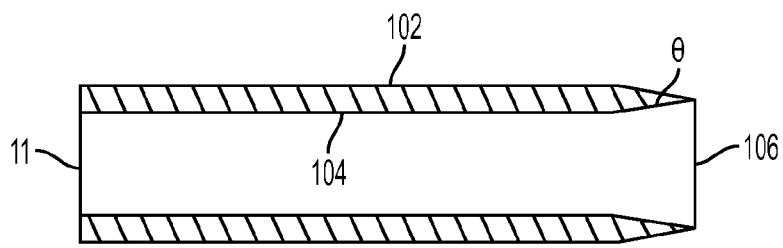
FIG. 13C
          
FIG. 13D                FIG. 13E

DEVICES, SYSTEMS, AND METHODS FOR TREATING HEART FAILURE

CROSS REFERENCE TO RELATED APPLICATION

This application claims the benefit of and priority to U.S. Provisional Patent Application No. 61/778,382, filed on Mar. 12, 2013. The entire content of the provisional application is incorporated herein by reference.

FIELD OF THE INVENTION

The present teachings relate to devices and methods of use thereof for treating heart failure. An example of the present teachings relates to a device that creates a shunt between two heart chambers thereby allowing blood flow from one to another heart chamber, changing (e.g. reducing) the blood pressure in a heart chamber. The present teachings further relate to devices and methods of use thereof to deliver such a device.

BACKGROUND

Congestive heart failure (CHF) is a condition affecting millions of people worldwide. CHF results from a weakening or stiffening of the heart muscle that commonly is caused by myocardial ischemia (due to, e.g., myocardial infarction) or cardiomyopathy (e.g., myocarditis, amyloidosis). CHF causes reduced cardiac output and inadequate blood to meet the needs of body tissue.

Treatments for CHF include: (1) pharmacological treatments, (2) assisting systems, and (3) surgical treatment. Pharmacological treatments, e.g., with diuretics, are used to reduce the workload of a heart by reducing blood volume and preload. While drug treatment improves quality of life, it has little effect on survival. Assisting devices, e.g., mechanical pumps, are used to reduce the load on the heart by performing all or part of the pumping function normally done by the heart. However, in a chronic ischemic heart, high-rate pacing may lead to increased diastolic pressure, calcium overload, and damage to the muscle fibers. There are at least three surgical procedures for treating a heart failure: (1) heart transplant, (2) dynamic cardiomyoplasty, and (3) the Batista partial left ventriculectomy. These surgical treatments are invasive and have many limitations.

CHF is generally classified into systolic heart failures (SHF) or diastolic heart failures (DHF). In a SHF, the pumping action of a heart is reduced or weakened. A normal ejection fraction (EF), which is a function of the volume of blood ejected out of the left ventricle (stroke volume) divided by the maximum volume remaining in the left ventricle at the end of the diastole or relaxation phase, is greater than 50%. In systolic heart failure, the EF is decreased to less than 50%. A patient with SHF may have an enlarged left ventricle because of cardiac remodeling developed to maintain an adequate stroke-volume. This pathophysiological phenomenon is often associated with an increased atrial pressure and a left ventricular filling pressure.

DHF is a heart failure without any major valve disease even while the systolic function of the left ventricle is preserved. Generally, DHF is failure of the ventricle to adequately relax and expand, resulting in a decrease in the stroke volume of the heart. Presently, there are very few treatment options for patients suffering from DHF. DHF afflicts between 30% and 70% of those patients with CHF.

There are several known techniques that can be used to treat the symptoms of DHF. Without attempting to characterize the following references, for example, U.S. Pat. No. 8,091,556 by Keren et al. discloses the use of an interatrial pressure relief shunt with a valve and a tissue affixation element at each end of the shunt; and United States Patent Application Publication No. 20050165344 by Dobak discloses a pressure relief system with an interatrial septal conduit with an emboli barrier or trap mechanism to prevent cryptogenic stroke due to thrombi or emboli crossing the conduit into the left sided circulation. Dobak also discloses a conduit with a one-way valve which directs blood flow from the left atrium to the right atrium.

The constantly evolving nature of heart failure represents a significant challenge for treatment. Therefore, there is a need for novel and adaptable methods and devices for treating DHF, for example, by creating a pressure relief shunt which can be retrieved, repositioned, adjusted, expanded, contracted, occluded, sealed and/or otherwise altered as required to treat the patient.

SUMMARY

One aspect of the present teachings provides devices for regulating blood pressure in a heart chamber. In various embodiments, the device for regulating blood pressure includes a transeptal tissue coring device for removing tissue from the heart, comprising a tissue incising element and a tissue stabilizer. In some embodiments, the tissue incising element comprises a proximal portion, a distal portion with a sharp edge at the distal end, and a longitudinal lumen extending from the proximal portion to the distal portion. In some embodiments, the tissue stabilizer comprises an elongated body, a distal portion, and a plurality of tissue supporting struts at the distal portion. In certain embodiments, the plurality of tissue supporting struts each comprises a fixed end attached to the elongated body and a free end configured to move radially away from the elongated body of the tissue stabilizer.

In various embodiments, the tissue stabilizer is slidably disposed within the longitudinal lumen of the tissue incising element. In some embodiments, the tissue supporting struts are stowed radially along the elongated body of the tissue stabilizer when the distal portion of the tissue stabilizer is constrained within the longitudinal lumen of the tissue incising element. In other embodiments, the tissue supporting struts expand radially to form a tissue supporting surface when the distal portion of the tissue stabilizer is exposed outside of the longitudinal lumen of the tissue incising element.

In various embodiments, a transseptal tissue coring device for removing tissue from the heart comprises a tissue incising element and a tissue stabilizer. In some embodiments, the tissue stabilizer comprises an elongated body, a distal portion, and a plurality of tissue supporting struts at the distal portion. In certain embodiments, the tissue supporting struts are formed by a plurality of slits along the elongated body of the tissue stabilizer.

In various embodiments, the tissue stabilizer is slidably disposed within the longitudinal lumen of the tissue incising element. In some embodiments, the tissue supporting struts are lengthened along the elongated body of the tissue stabilizer when the distal portion of the tissue stabilizer is constrained within the longitudinal lumen of the tissue incising element. In other embodiments, the tissue supporting struts are shortened and expand radially to form a tissue supporting surface when the distal portion of the tissue stabilizer is exposed outside of the longitudinal lumen of the tissue incising element.

Another aspect of the present teachings provides a method of percutaneously removing tissue from the heart. In various embodiments, the method comprises providing a transseptal tissue coring device comprising a tissue incising element with a sharp edge at a distal end and a tissue stabilizer having a plurality of tissue supporting struts at a distal portion of the tissue stabilizer where the tissue stabilizer is slidably disposed within an elongated lumen of the tissue incising element; advancing the transseptal tissue coring device to a proximity of the atrial septum; expanding the tissue supporting struts of the tissue stabilizer radially and positioning the tissue stabilizer against the atrial septum inside the left atrium; advancing the tissue incising element distally so that the sharp edge at the distal end of the tissue incising element is positioned against the atrial septum inside the right atrium; making an incision in the atrial septum by using the tissue incising element and/or the tissue stabilizer; and retracting the tissue stabilizer proximally, allowing the distal portion of the tissue stabilizer to slide back into the tissue incising element and the tissue supporting struts carrying the removed septal tissue to fold radially and distally, where the removed septal tissue is captured inside the elongated lumen of the tissue incising element.

Another aspect of the present teachings provides a method of percutaneously removing tissue from the heart. In various embodiments, the method comprises providing a delivery sheath and a transseptal tissue coring device, wherein the delivery sheath comprises a distal end and a longitudinal lumen, the transseptal tissue coring device is slidably disposed within the longitudinal lumen of the delivery sheath, wherein the transseptal tissue coring device comprises a tissue incising element with a sharp edge at a distal end and a tissue stabilizer having a plurality of tissue supporting struts at a distal portion, where the tissue stabilizer is slidably disposed within an elongated lumen of the tissue incising element; advancing the transseptal tissue coring device to a proximity of the atrial septum; expanding the tissue supporting struts of the tissue stabilizer radially and positioning the tissue stabilizer against the atrial septum inside the left atrium; advancing the tissue incising element distally so that the sharp edge at the distal end of the tissue incising element is positioned against the atrial septum inside the right atrium; incising the septal tissue using the tissue incising element and/or the tissue stabilizer; advancing the delivery sheath distally so that the distal end of the delivery sheath is at the proximity of the atrial septal tissue; retracting the tissue incising element proximally; and retracting the tissue stabilizer proximally to allow the distal portion of the tissue stabilizer to slide back into the delivery sheath and the tissue supporting struts carrying the removed septal tissue to fold radially and distally, wherein the removed septal tissue is captured inside the elongated lumen of the tissue incising element.

BRIEF DESCRIPTION OF THE DRAWINGS

FIG. 2 is a perspective view of the exemplary medical device of FIG. 1 in a constrained configuration.

FIGS. 3A-3C are perspective views of the exemplary medical device of FIG. 2 in accordance with the present teachings.

FIGS. 13A-13E are perspective views of an exemplary embodiment of a tissue incising element in accordance with the present teachings.

DETAILED DESCRIPTION

Figure 1:
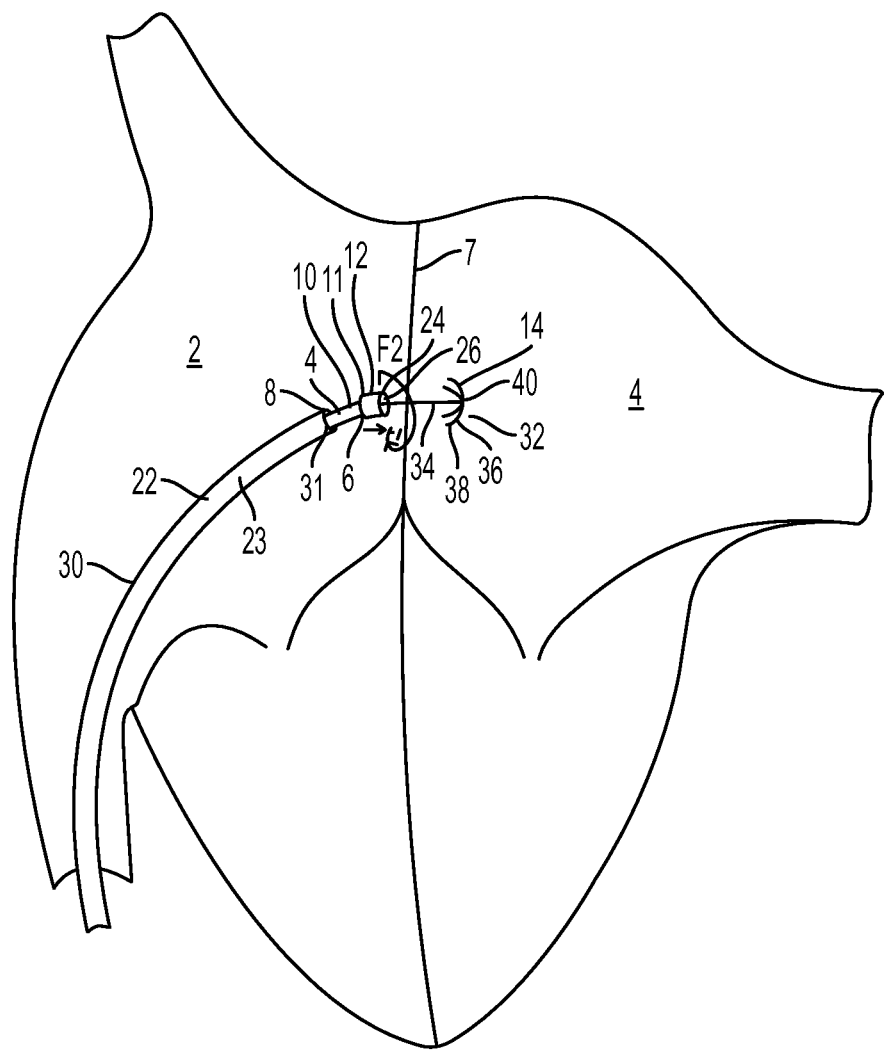
FIG. 1 is a perspective view of an exemplary medical device in accordance with the present teachings.

Certain specific details are set forth in the following description and drawings to provide an understanding of various embodiments of the present teachings. Those with ordinary skill in the relevant art will understand that they can practice other embodiments of the present teachings without one or more of the details described below. Finally, while various processes are described with reference to steps and sequences in the following disclosure, the steps and sequences of steps should not be taken as required to practice all embodiments of the present teachings.

As used herein, the terms "radially outward" and "radially away" means any direction which is not parallel with the central axis. For example, considering a cylinder, a radial outward member could be a piece of wire or a loop of wire that is attached or otherwise operatively coupled to the cylinder that is oriented at an angle greater than 0° relative to the central longitudinal axis of the cylinder.

As used herein, the term "lumen" means a canal, duct, generally tubular space or cavity in the body of a subject, including veins, arteries, blood vessels, capillaries, intestines, and the like. The term "lumen" can also refer to a tubular space in a catheter, a sheath, or the like in a device.

As used herein, the term "proximal" shall mean closest to the operator (less into the body) and "distal" shall mean furthest from the operator (further into the body). In positioning a medical device inside a patient, "distal" refers to the direction away from a catheter insertion location and "proximal" refers to the direction near the insertion location.

The exemplary devices described in various embodiments each is used to create an aperture or a shunt on the atrial septum, which allows fluid communication between the left and right atria and releases the left atrium pressure. It, however, should be appreciated that the present teachings are also applicable for use in other parts of the anatomy, or for other indications. For instance, a device, such as one described in the present teachings, could be used to create a shunt between the coronary sinus and the left atrium for the same indication. Additionally, a shunt such as one described in the present teachings could be placed between the azygous vein and the pulmonary vein.

The following description refers to FIGS. 1 to 14. A person with ordinary skill in the art would understand that the figures and description thereto refer to various embodiments of the present teachings and, unless indicated otherwise by their contexts, do not limit the scope of the attached claims.

The present teachings relate to a transseptal tissue coring device and methods of using such a device for percutaneously removing a certain size and/or amount of tissue from the atrial septum, producing an aperture in the atrial septum, and creating a left-to-right blood shunt in the atria. In some embodiments, the device includes an elongated tubular body with a tissue incising element at its distal end and a tissue stabilizer slidably disposed within the tubular lumen of the elongated body during delivery. The tissue stabilizer is configured to extend through an aperture on the septum, stabilize, and support the septum from the opposite side of an incision as described herein.

According to various embodiments, the tissue incising element is adapted at the distal end of the elongated tubular body. In some embodiments, the tissue incising element includes a proximal end, a distal end, and a body extending between the proximal end and the distal end. In some embodiments, the proximal end of the tissue incising element attaches to the distal end of the elongated tubular body and the distal end of the tissue incising element includes a sharp edge along the circumference configured for incising tissue. In some embodiments, the body of the tissue incising element has a tubular shape. In other embodiments, the body of the tissue incising element has a collapsible cone shape.

In various embodiments, a tissue stabilizer of the present teachings includes an elongated body with a distal portion and a proximal portion. In some embodiments, the distal portion of the tissue stabilizer has at least two radially expandable tissue supporting struts. In various embodiments, the tissue stabilizer has a pre-formed radially expanded configuration and a stowed configuration.

In various embodiments, a transseptal tissue coring device of the present teachings tracks over a guide wire, for example, positioned across a tissue beforehand. In some embodiments, the tissue stabilizer includes a tissue piercing element. For example, the tissue piercing element can be used to create an aperture on the septum.

In various embodiments, a transseptal tissue coring device of the present teachings includes an elongated delivery profile where the tissue supporting struts of the tissue stabilizer are stowed radially inward so that the entire tissue stabilizer is slidably disposed within the elongated lumen of the elongated member. In other embodiments, the transseptal tissue coring device includes an expanded deployed profile where the tissue stabilizer is exposed distally outside of the tissue incising element and the tissue supporting struts expand radially.

In various embodiments, a tissue coring device of the present teachings is configured to be percutaneously delivered into the right atrium, across the atrial septum, and inside the left atrium. In some embodiments, the tissue stabilizer supports a piece of septal tissue while the tissue incising element incises the tissue. In some embodiments, the tissue stabilizer captures and percutaneously removes the detached tissue from the body. In such embodiments, the aperture generated with the tissue coring device described herein allows blood flow from one side of the septum to the other. In some embodiments, the aperture has a minimum size of 3-4 mm in general diameter, so that the aperture will not heal itself, i.e. re-closure, over time, thereby allowing a continuous pressure relief to the left heart over time. In various other embodiments, the device is used with a delivery system.

FIG. 1 shows an exemplary embodiment of a transseptal tissue coring device (10) deployed inside a heart according to the present teachings. As illustrated in FIG. 1, the transseptal tissue coring device (10) includes an elongated tubular body (8) with a tissue incising element (12) connected at its distal end (6) and a tissue stabilizer (14). The elongated tubular body (8) has a proximal end (not shown), a distal end (6), and a central lumen (4) extending from the proximal end to the distal end (6). The tissue incising element (12) has a proximal end (11), a distal end (24), and an axial lumen (26). The proximal end (11) of the tissue incising element (12) is attached to the distal end (6) of the elongated tubular body (8) by a mechanical, chemical, thermal, or other mechanism known to those in the field. The distal end (24) of the tissue incising element (12) has a cutting edge. The axial lumen (26) of the tissue incising element (12) joins the central lumen (23) of the elongated tubular body (8) to form a continuous conduit. The tissue stabilizer (14) is slidably disposed within the axial lumen (26) of the tissue incising element (12). The tissue stabilizer (14) has an elongated body (34) with a proximal portion (not shown) and a distal portion (32). The distal portion (32) of the tissue stabilizer (14) has a tissue supporting/gripping element. In this particular embodiment, the tissue supporting/gripping element includes a plurality of struts (36) each with its fixed ends (40) connected to the elongated body (34) of the tissue stabilizer (14) and its free ends (38) extending radially outward from the elongated body (34) of the tissue stabilizer (14).

In some embodiments, the tissue coring device is percutaneously delivered via a delivery sheath (30). The delivery sheath (30) includes a proximal end (not shown), a distal end (31), and a longitudinal lumen (22). As described herein, the tissue coring device (10) includes an elongated delivery profile, a deployed profile, and a collapsed tissue retrieval profile. In its delivery profile, the entire tissue coring device (10) is slidably disposed within the lumen (22) of the delivery sheath (30). In its deployed profile, the tissue coring device (10) extends distally and the tissue incising element (12) and the tissue supporting/gripping element each exits outside of the lumen (22) of the delivery sheath (30) and resume its intended configuration. In its tissue retrieval profile, the tissue incising element (12) is pulled proximally back inside the lumen (22) of the delivery sheath (30) and the tissue supporting/gripping element collapses and is pulled proximally inside the lumen (26) of the tissue incising element (12) and/or the lumen (22) of the delivery sheath (30).

In some embodiments, the tissue incising element and the tissue stabilizer are incorporated with radiopaque markers so the devices may more easily be visualized using a radiographic imaging equipment such as with x-ray or fluoroscopic techniques. In some other embodiments, the entire transseptal tissue coring device is made of a radiopaque material. In some embodiments, the radiopaque marker/material is made of tantalum, tungsten, platinum irridium, gold, alloys of these materials or other materials that are known to those skilled in the art. In other embodiments, radiopaque markers comprising cobalt, fluorine or numerous other paramagnetic materials or other MR visible materials that are known to those skilled in the arts are incorporated in the tissue incising element and/or the tissue stabilizer. In certain embodiments, the paramagnetic material or MR visible material is incorporated with a radiopaque material. For example, two or more of a paramagnetic material, a MR visible material, an X-ray material, or a fluoroscopic material, each of which is described herein, can be arranged in alternating locations on the device to enable both x-ray and MR imaging of the device.

FIG. 1 illustrates one embodiment of the tissue stabilizer (14). According to this embodiment, the tissue supporting struts (36) of the tissue stabilizer (14) extend outside of the distal end (24) of the tissue incising element (12). For example, the elongated body (34) of the tissue stabilizer (14) extends distally so that the tissue supporting struts (36) extend outside of the axial lumen (26) of the tissue incising element (12). Although not shown in FIG. 1, the proximal end and the movement of the elongated body (34) is controlled by a clinician from outside of the body. FIG. 1 further illustrates an embodiment of the tissue stabilizer (14) deployed inside the left atrium (4) with the elongated body (34) of the tissue stabilizer (14) across the atrial septum (7) and the tissue supporting struts (36) of the tissue stabilizer (14) expanding radially outward. FIG. 1 further illustrates that the distal end (24) of the tissue incising element (12) is within the right atrium (2) and at a proximity to the atrial septum (7). FIG. 1 further illustrates one exemplary tissue incising element (12) having a tubular shaped body.

FIG. 2 shows an exemplary transseptal tissue coring device (10) having a distal portion in an elongated delivery profile. According to some embodiments, the tissue supporting/gripping element are held within the lumen (26) of the tissue incising element (12) or the lumen (4) of the elongated body (8) of the tissue coring device (10). According to this particular embodiment in FIG. 2, the tissue supporting struts (36) are stowed inward radially and the distal portion (32) of the tissue stabilizer (14) is disposed within the axial lumen (26) of the tissue incising element (12). In such an embodiment, the tissue supporting struts (36) of the tissue stabilizer (14) fold radially inward so that the free ends (38) of the struts (36) are tugged close to the longitudinal axis of the elongated body (34) of the tissue stabilizer (14). In one embodiment, the tissue supporting struts (36) are folded inward proximally so that the free ends (38) are tugged proximally to the fixed end (40), as seen in FIG. 2. In other embodiments, the tissue supporting struts (36) are folded inward distally so that the free ends (38) is tugged distally to the fixed end (40). In some embodiments, in its delivery profile, the tissue stabilizer (14) slides from the proximal end of the lumen (4) of the elongated tubular body (8) distally and to the axial lumen (26) of the tissue incising element (12). In another embodiment, the tissue stabilizer (14) is pre-loaded inside the axial lumen (26) of the tissue incising element (12) and both the elongated tubular body (8) and the tissue incising element (12) holding the tissue stabilizer (14) inside its axial lumen (26) are delivered via a delivery sheath into the heart. The tissue stabilizer (14) transitions from its stowed delivery profile to an expanded deployed profile, such as shown in FIGS. 3A-3C, when it extends distally outside of the lumen (26) of the tissue incising element (12).

According to another embodiment, the tissue stabilizer (14) can also be slidably disposed within a separate sheath which can slide through the conduit funned by the elongated body (8) and the tissue incising element (12). In such an embodiment, the tissue stabilizer (14) is deployed distally further away from the tissue incising element (12). One example of such a sheath (33) is shown in FIG. 3A.

FIGS. 3A-C illustrate an exemplary transseptal tissue coring device according to the present teachings. FIGS. 3A-C show the distal portion of the transseptal tissue coring device (10) in the deployed profile, where the distal portion (32) of the tissue stabilizer (14) is extended outside of the tissue incising element (12) and the tissue supporting struts (36) expand radially outward to form a tissue supporting surface. In some embodiments, the tissue supporting surface is substantially planar and is substantially parallel to the atrial septum, as illustrated in FIG. 3A. In other embodiments, the tissue supporting surface has a concave shape or a sloped shape as shown in FIG. 3B, where the free ends (38) of the struts (36) are proximal to the fixed ends (40) of the struts (36). In yet other embodiments, the tissue supporting surface has a convex shape or a sloped shape as shown in FIG. 3C, where the free ends (38) of the struts (36) are distal to the fixed ends (40) of the struts (36). One with ordinary skill in the art would also understand that the radially expanded struts (36) can form a tissue supporting surface with any shapes and forms and disclosure of various embodiments of the present teachings should not be viewed as limiting.

According to some embodiments, during a tissue retrieval as described herein, the tissue stabilizer (14) is pulled proximally back inside the axial lumen (26) of the tissue incising element (12) from the distal end (24) of the tissue incising element (12); and, constrained by the lumen of the tissue incising element (12), the tissue supporting struts (36) fold distally inward and the tissue stabilizer (14) resumes the elongated profile. Alternatively, the tissue stabilizer (14) is pulled proximally into the lumen of a sheath from its distal end and, constrained by the sheath, the tissue supporting struts (36) fold distally inward and the tissue stabilizer (14) resumes its elongated profile.

Figure 4A:
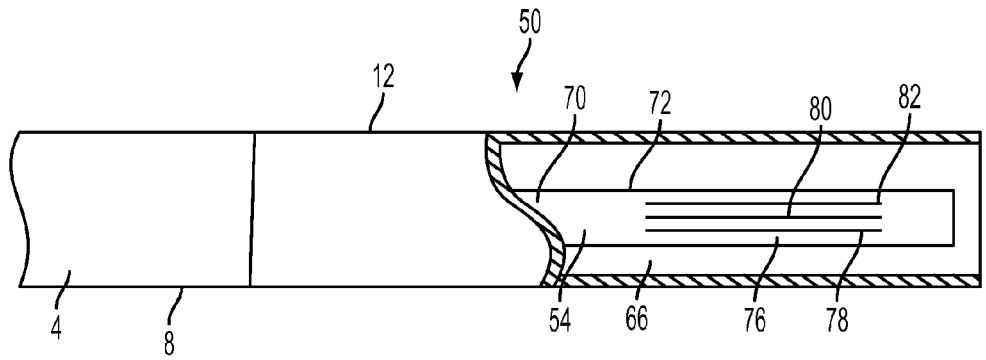
FIGS. 4A-4B are perspective views of an exemplary medical device in a constrained configuration.

FIGS. 4A-D illustrate several other exemplary tissue supporting struts (76) in their delivery and deployed profiles. In FIG. 4A, the distal portion of the transseptal tissue coring device (50) is in an elongated delivery profile, where the tissue supporting struts (76) are constrained inward radially and the distal portion (72) of the tissue stabilizer (54) is disposed within the axial lumen (26) of the tissue incising element (12). In this embodiment, the tissue stabilizer (54) has a generally tubular body (70) with a proximal portion (not shown), a distal portion (72), and a central lumen (74) extending in between. The distal portion (72) of the tube forms tissue supporting struts (76). As seen in FIG. 4A, the distal portion (72) of the tube has a plurality of slits (78). Each slit (78) extends from a first location (80) to a second location (82) on the distal portion (72) of the tubular body (70). In one embodiment, the slits (78) have equal length, are parallel to one another, and are parallel to the longitudinal axis of the tubular body (70). In another embodiment, at least two slits (78) have different lengths from each other.

Figure 4B:
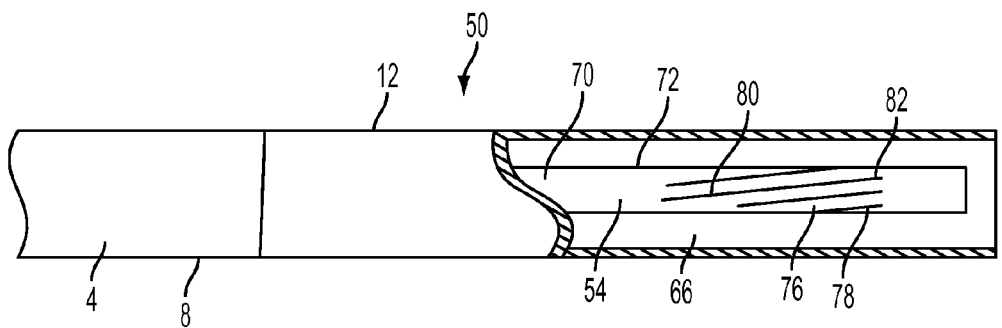

In an alternative embodiment, slits (78) may be cut at an angle such that they are helically disposed along the tubular body (70), as illustrated in FIG. 4B. In one embodiment, slits are straight. In another embodiment, slits (78) are not straight. For example, slits (78) may be zigzag, S-shaped, or C-shaped. One reasonably skilled in the art would be capable of selecting a shape and/or angle suitable for a given clinical application without any undue experimentation. In one embodiment, a strut (76) is formed between two slits (78) radially next to each other.

Figures 4C, 4D:
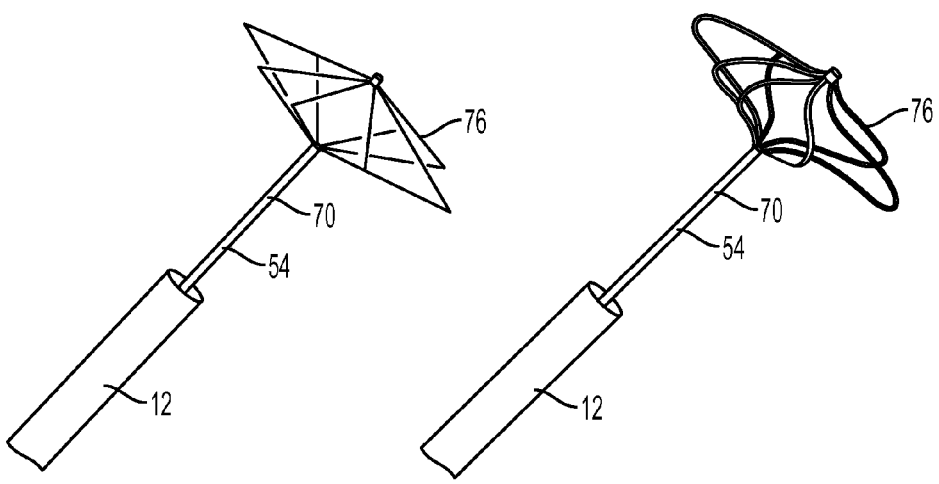
FIGS. 4C-4D are perspective views of the exemplary medical device of FIGS. 4A-4B in accordance with the present teachings.

FIGS. 4C-D illustrate another embodiment of the transseptal tissue coring device (50) with its distal portion in a deployed profile. In this embodiment, the distal portion (72) of the tissue stabilizer (54) is extended outside of the axial lumen (26) of the tissue incising element (12) and the tissue supporting struts (76) expand radially outward and form a tissue supporting surface. As illustrated in FIG. 4C, in one embodiment, as the tissue supporting struts (76) become free from the constraint of the tissue incising element (52), the axial length of the distal portion (72) of the tubular body (70) is reduced, the struts (76) between the slits (78) are folded longitudinally to form tissue supporting struts (76), and the tissue supporting struts (76) form a tissue supporting surface. As illustrated in FIG. 4I), in another embodiment, the struts (76) between slits (78) twist to form a tissue supporting surface. Similar to those illustrated in FIGS. 3A-C, the tissue supporting surface can be substantially planar, generally curved or sloped toward the septum, or generally curved or sloped away from the septum. Additionally, the tissue stabilizer (54) can also slidably be disposed within a separate sheath, which can slide through the conduit formed by the elongated body (8) and the tissue incising element (12).

According to some embodiments, during a tissue retrieval described herein, the tissue stabilizer (54) is pulled proximally back inside the axial lumen (26) of the tissue incising element (12) from its distal end (24) and, constrained by the tissue incising element, the tissue supporting struts (76) fold inward radially and the tissue stabilizer resumes its elongated profile. In an alternative embodiment, during tissue retrieval, the deployed tissue supporting struts (76) are forced by the distal end of the tissue incising element or a retrieval sheath to stretch longitudinally and reduce its profile as it is pulled proximally into the axial lumen of the tissue incising element or the sheath.

Although specific slitting patterns and shapes have been described here, one reasonably skilled in the art would understand that other designs can be incorporated without any undue experimentation to form a tissue stabilizer so long as each of such designs provides an elongated delivery profile and an expanded deployed profile. Thus, the specific embodiments described herein should not be viewed as limiting.

According to some embodiments, the tissue supporting struts (36, 76) transition from an elongated delivery profile to an expanded deployed profile by elastic recovery or thermal-shape transformation. In some embodiments, if a sufficiently elastic and resilient material is used, the struts (36, 76) can be pre-formed into the deployed shape and then elastically deformed and stowed during delivery. After the device is successfully delivered, it recovers to the preformed shape by the elastically recovery. In other embodiments, the tissue supporting struts (36, 76) may be manually expanded to the desired deployment shape and heat set in an oven while maintained in such a desired shape to memorize the shape. The struts (36, 76) are then distorted into a generally straightened profile during a delivery process and resume their intended deployed profile in vivo. In some embodiments the tissue supporting struts may be distorted from a generally straightened profile to their intended deployed profile in vivo by use of a wire attached to the most distal end. For example, the struts can be distorted into the deployed profile by moving the wire proximally to reduce the axial length of the distal portion and move the struts radially outward.

According to various embodiments, the tissue stabilizer includes at least two tissue supporting struts (36, 76). Devices according to the present teachings may include any number of tissue supporting struts (36, 76). In some embodiments, the tissue stabilizer includes eight tissue supporting struts (36, 76), as illustrated in FIGS. 3A-C and FIGS. 4A-D. Devices having between four and ten tissue supporting struts (36, 76) can be made without any significant changes in the processes described herein. A person with ordinary skill in the art can determine the appropriate number of tissue supporting struts (36, 76) based on a variety of anatomical and manufacturing factors.

According to some embodiments, during a tissue coring, the tissue stabilizer (14, 54) is deployed and positioned against one side of the tissue and the tissue incising element (12, 52) is deployed and positioned against the opposite side of the tissue. Thus, the tissue stabilizer (14, 54) provides support to the septal tissue during a tissue coring. In some embodiments, the deployed tissue stabilizer (14, 54) has a general size greater than the general size of the surface formed by the cutting edge of the tissue incising element (12, 52) so that a substantial area of the tissue to be cut is supported by the tissue supporting struts (36, 76). In some embodiments, the deployed tissue supporting struts form a surface 50-4000% greater than the surface formed by the cutting edge of the tissue incising element (12, 52). In some embodiments, the deployed tissue supporting struts (36, 76) form a surface with a general diameter of 5 mm to 25 mm. In other embodiments, the deployed tissue supporting struts (36, 76) form a tissue supporting surface with a general diameter 50-600% greater than the general diameter of the surface formed by the cutting edge of the tissue incising element (12, 52).

Figure 5A:
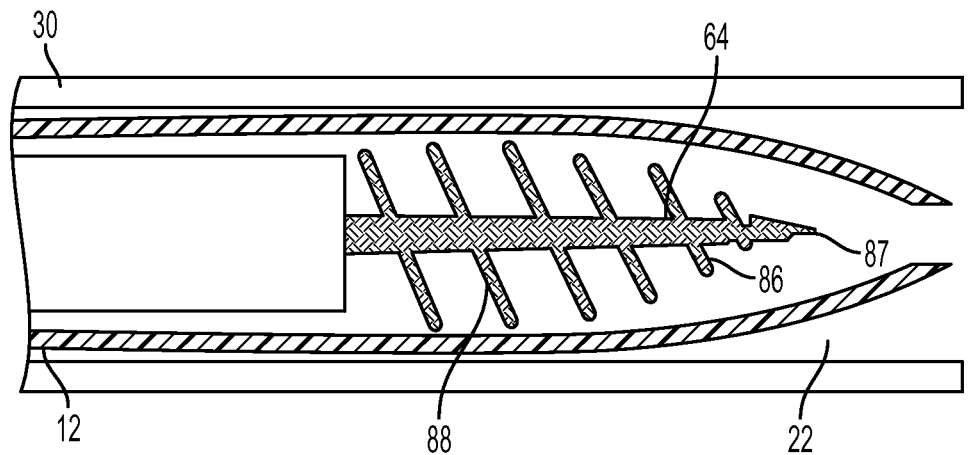
FIGS. 5A-5B are perspective views of the exemplary medical device in accordance with the present teachings.
Figure 5B:
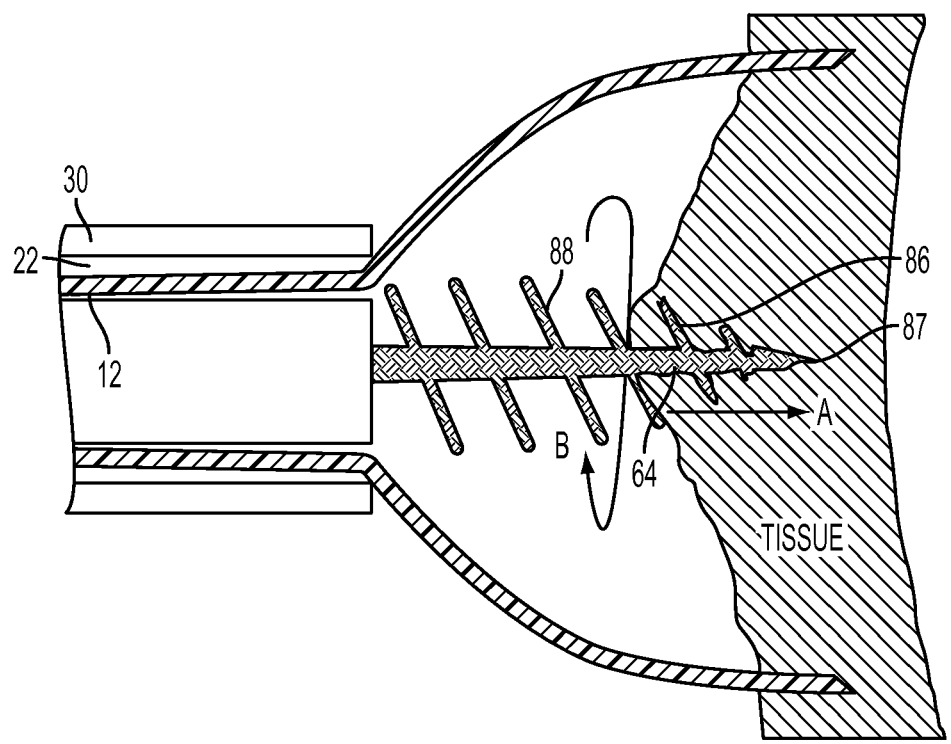

FIGS. 5A-5B further illustrate another embodiment of the tissue stabilizer (64) in a transseptal curing device of the present teachings. In some embodiments, the tissue stabilizer (64) has an elongated body (84) with a tissue gripping element (86) at its distal end. In these embodiments, the tissue gripping element has a helical screw like profile (88) with a short and sharp tip (87) for initial tissue engagement. In one embodiment, the tissue stabilizer (64) is advanced distally as indicated by arrow A to allow the tip (87) to engage and grip the tissue. A clinician then rotates the tissue stabilizer (64) as indicated by arrow B to allow the helical screw (88) to further dig into the tissue as shown in FIG. 5B. FIG. 5A shows a delivery profile of the tissue stabilizer (64), specifically, the helical screw like profile (88) held within the lumen of the tissue incising element (12) and the entire tissue coring device held within the lumen (22) of the sheath (30). FIG. 5B shows a deployed profile of the tissue stabilizer (64) where it is advanced distally outside of the lumen (22) of the sheath (30) and engages tissue. One skilled in the art can incorporate any suitable diameter, taper, pitch, lead, and/or thread design in designing and making the helical screw like profile (88) without any undue experimentation. According to some embodiments, during tissue retrieval, the deployed tissue gripping element simply carries the removed tissue, retract proximally, and enter the axial lumen of the tissue incising element or the sheath.

Figure 6A:
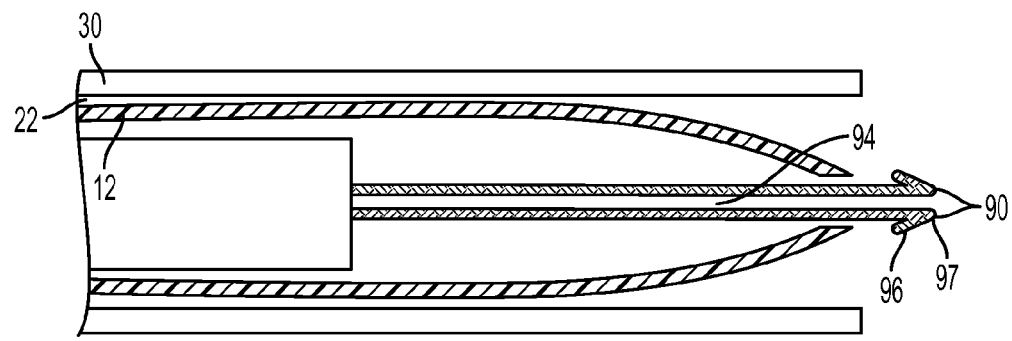
FIGS. 6A-6B are perspective views of the exemplary medical device in accordance with the present teachings.
Figure 6B:
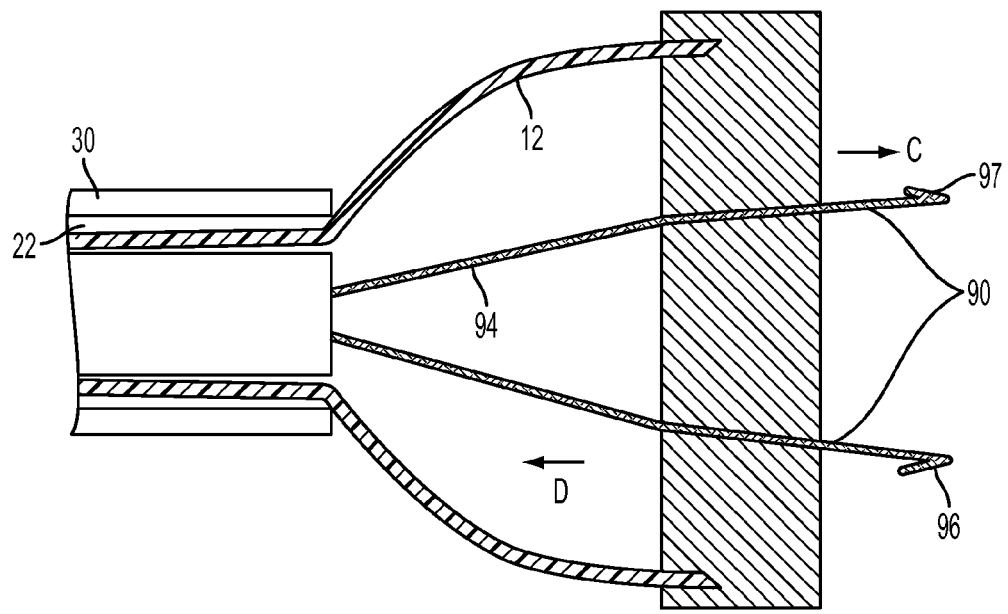

FIGS. 6A-6B further illustrate another embodiment of the tissue stabilizer (94). According to this embodiment, the tissue stabilizer (94) includes an elongated body (92) with a tissue gripping element (90) at its distal end. In addition, the tissue gripping element includes a sharp distal tip (97) for piercing tissue and multiple barb-like elements (96) with reversed hooks (98) at its distal end to engage and secure tissue. In one embodiment, to engage and grip tissue, the tissue stabilizer (94) is advanced distally as indicated by arrow C to allow the tip (97) to pierce the tissue and enter into the opposite side. The tissue stabilizer (94) is then withdrawn proximally, as indicated by arrow D, such that the reversed hooks (98) engage the tissue. FIG. 6A shows a delivery profile of the tissue stabilizer (94) where the helical screw like profile (88) is held within the lumen of the tissue incising element (12) and the tissue coring device is held within the lumen (22) of a sheath (30). FIG. 6B shows the deployed profile of the tissue stabilizer (94) where it is advanced distally outside of the lumen (22) of the sheath (30) and engages tissue. According to some embodiments, during tissue retrieval, the deployed tissue gripping element simply carries the removed tissue, collapse radially, retracts proximally, and enters the axial lumen of the tissue incising element or the sheath.

The tissue stabilizer (14, 54, 64, 94) can be made of a biocompatible metal or polymer. In some embodiments, the tissue stabilizer (14, 54, 64, 94) in whole or in part is made of an elastic material, a super-elastic material, or a shape-memory alloy which allows selected portions to distort into a generally straightened profile during the delivery process and resume and maintain its intended profile in vivo once deployed. In some embodiments, part or all of the tissue stabilizer (14, 54, 64, 94) is made of stainless steel, nitinol, Titanium, Elgiloy, Vitalium, Mobilium, Ticonium, Platinore, Stellite, Tantalum, Platium, Hastelloy, CoCrNi alloys (e.g., trade name Phynox). MP35N, or CoCrMo alloys or other metallic alloys. Alternatively, in such other embodiments, part or the entire device is made of a polymer such as PTFE, UHMPE, HDPE, polypropylene, polysulfone, polymethane, Pebax® or another biocompatible plastic.

FIGS. 1-12 illustrate various embodiments of a tissue incising element of the present teachings. According to some embodiments, the tissue incising element includes a distal end, a proximal end, an extended body between the distal end and the proximal end, an axial lumen through the entire length of the tissue incising element, and a luminal surface. In some embodiments, the proximal end of the tissue incising element joins the distal end of the elongated body (8). In some embodiments, the axial lumen of the tissue incising element joins the central lumen (23) of the elongated tubular body (8) and the axial lumen and the central lumen (23) form a continuous conduit. In some embodiments, the overall size of the tissue incising element remains the same during the percutaneous delivery and tissue removal processes. According to other embodiments, the tissue incising element has a compressed small diameter configuration during the percutaneous delivery, an expanded large diameter (at least at the distal end of the tissue incising element) deployed configuration during the tissue incision, and a collapsed small diameter configuration when the tissue incision element is removed from the body ("device retrieval"). In certain embodiments, the diameter at the distal end of the tissue incision element during the tissue incision process is up to 400% of that during the percutaneous delivery or device retrieval processes. According to other embodiments, the tissue incising element is configured to transition from the delivery configuration to the deployed configuration via an elastic transformation, a thermal transformation, a mechanical actuation, or other means known to those skilled in the art.

In various embodiments, the tissue incising element is configured to move distally or proximally by a clinician from outside of the body. In various embodiments, the tissue incising element is configured to rotate clock-wise or counter clock-wise by a clinician from outside of the body. The mechanism for percutaneously moving a medical device and/or the tissue stabilizer distally or proximally or rotating the medical device in a clock-wise or counter clock-wise fashion are known in the art. In some embodiments, the tissue incising element also includes a cutting edge for removing tissue. The cutting edge and use thereof is discussed herein, including as shown in FIGS. 13A-13E.

In various embodiments, the cross section of the tissue incising element (12) is circular or polygonal, such as square or hexagonal. In some embodiments, the cross section of the tissue incising element (12) is substantially uniform throughout its length. In other embodiments, the cross section of the tissue incising element (12) varies throughout the length.

In various embodiments, the tissue is removed by the a direct force "F1", as shown in FIG. 1, applied by the tissue incising element against the deployed tissue stabilizer (14, 54). In various other embodiments, the septal tissue is removed by a torque "F2", as shown in FIGS. 2 and 14D, by rotating the tissue incising element against the tissue stabilizer (14, 54). In yet other embodiments, the septal tissue is removed by a combination of a direct force "F1" and a torque "F2."

FIGS. 1-6 illustrate several exemplary tissue incising elements (12) according to the present teachings. In various embodiments, the tissue incising element (12) includes a distal end (24), a proximal end, and a tubular body with an axial lumen (26) and a continuous luminal surface extending in between. In some embodiments, the tissue incising element (12) has an uniform diameter throughout its entire length. In various embodiments, the distal end of the tissue incising element (12) has a generally continuous sharp tissue cutting edge (106). In some embodiments, the proximal end (11) of the tissue incising element is capable of joining the proximal end of the elongated body (not shown) by a mechanical, a chemical, a thermal, or other mechanisms known to those in the field.

Figure 7A:
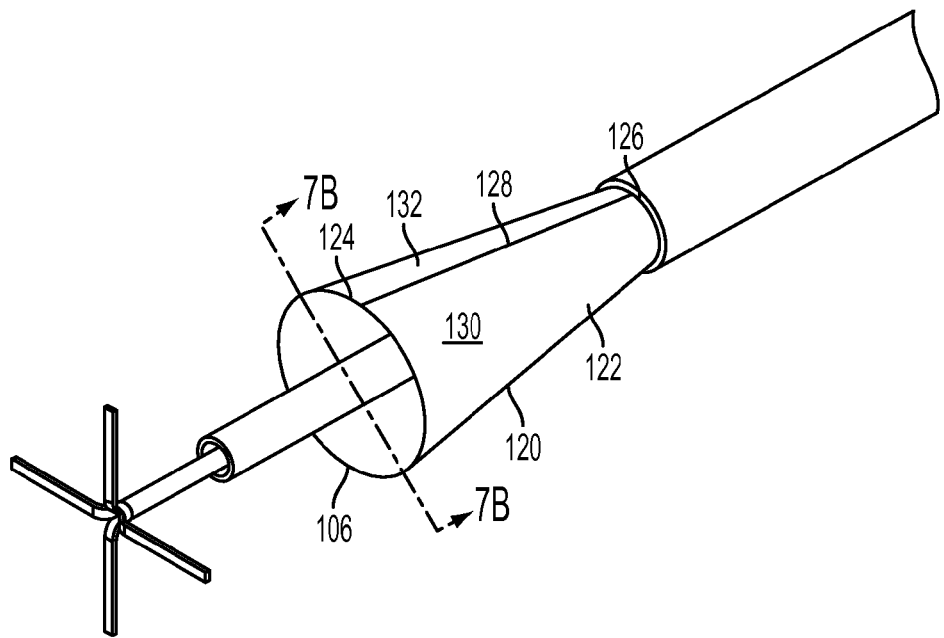
FIGS. 7A-7B are perspective views of the exemplary medical device in accordance with the present teachings.

FIG. 7A illustrates another embodiment of the present teachings, where the tissue incising element (120) is at its deployed configuration. At its deployment configuration, the tissue incising element (120) is expanded in the shape of a cone, a bell, a funnel, a trumpet, or any other shapes that provide a greater diameter. FIG. 7A illustrates an embodiment of the present teachings where the tissue incising element (120) has a preformed cone shaped body (122). In some embodiments, the preformed cone shaped body includes a wide base at the distal end (124) and a narrow base at the proximal end (126). In some embodiments, the tissue incising element (120) includes a generally continuous tissue cutting edge (106) at its distal end (124). In some embodiments, the tissue incising element includes a preformed funnel-shaped body with a radially expanded distal portion, a tubular shaped segment at the distal end of the distal portion, a shorter but more steeply angled cone at the proximal end of the distal portion, and a tissue cutting edge at the distal end. In various embodiments, the tissue incising element has a collapsed configuration where the tissue incising element is constrained by a sheath, the cone shaped body collapses to form an elongated shape with the proximal and distal ends of the incising element being generally the same size.

Figure 7B:
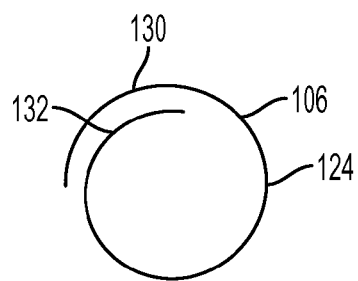

In various embodiments, the tissue incising element (120) is preformed into its expanded profile and can transition from its expanded profile to its collapsed profile. In some embodiments, the cone shaped body includes one or more slits (128) and one or more flaps (130, 132). In some embodiments, some of these slits (128) are along a portion or the entire length of the cone shaped body (122) of the tissue incising element (120). In some embodiments, portions of the adjacent flaps (130, 132) of the tissue incising element (120) overlap when the tissue incising element (120) is in its collapsed profile. FIG. 7B illustrate the distal end view of the tissue incising element (120) in the collapsed profile where flaps (130, 132) defined by the slits collapse inward and sections of the flaps overlap one another.

Figure 8:
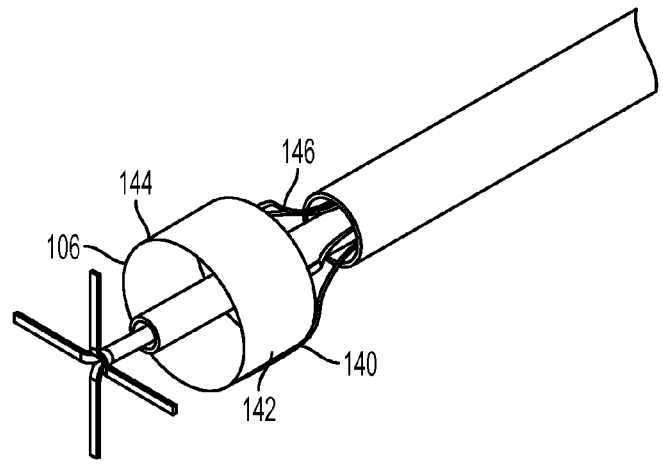
FIG. 8 is a perspective view of an exemplary medical device in accordance with the present teachings.

FIG. 8 illustrates another exemplary tissue incising element (140) at its deployed configuration. In this particular example, the tissue incising element (140) includes a preformed generally cylindrical shaped distal portion (142) and the distal portion includes a continuous luminal surface, a generally continuous tissue cutting edge (106) at the distal end (144), and a proximal tab (146) adapted to connecting the distal portion (142) of the tissue incising element (140) to the distal end of the elongated body (8) (not shown). Similar to what is described in FIG. 8, the tissue incising element (140) transitions from its deployed profile to its collapsed profile through various means or designs. For example, the tissue incising element (140) can have at least one longitudinal slit and at least two flaps, of which portions overlap when the tissue incising element (140) collapses into a smaller delivery profile. In certain embodiments, the distal portion (142) and the proximal tab (146) of the tissue incising element (140) are portions of a unitary piece out of a same material. In certain embodiments, the distal portion (142) and the proximal tab (146) of the tissue incising element (140) are separate pieces that are joined together.

Figures 9A, 9B:
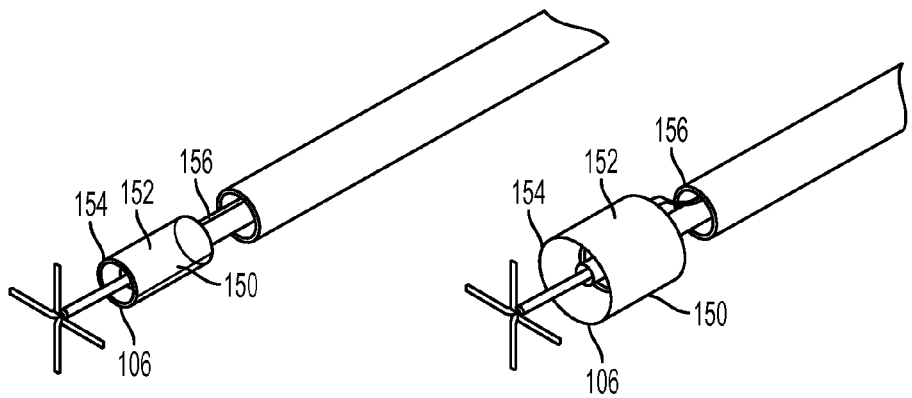
FIGS. 9A-9C are perspective views of an exemplary medical device in accordance with the present teachings.
Figure 9C:
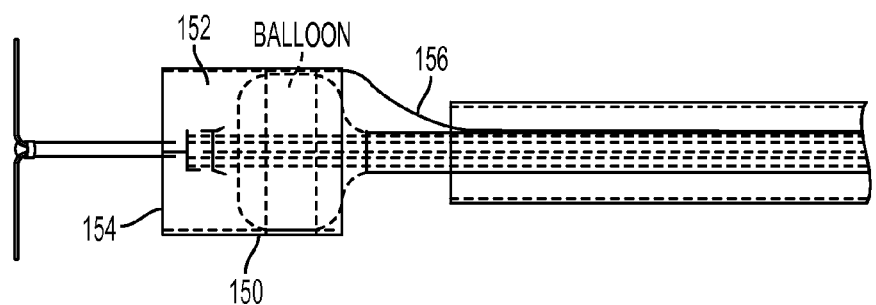

FIGS. 9A-9C illustrate another exemplary tissue incising element (150). Similar to what has been described in connection with FIG. 8, the tissue incising element (150) in its deployed configuration also includes an enlarged distal portion (152), a proximal tab (156), and a generally continuous tissue cutting edge (106) at the distal end (154). Unlike the embodiment illustrated in FIG. 8, the distal portion (152) of the tissue incising element (150) in this instance is preformed to a delivery profile adapted to be delivered through the sheath (30) as shown in FIG. 9A. Upon reaching the treatment site, the tissue incising element (150) extends outside of the sheath (30) and expanded manually, for example, by a balloon, as shown in FIGS. 9B and 9C. Similar to what has been described in connection with FIG. 8, the tissue incising element (150) has at least one longitudinal slit that facilitate a transition from the delivery profile to the deployed profile.

Figure 10:
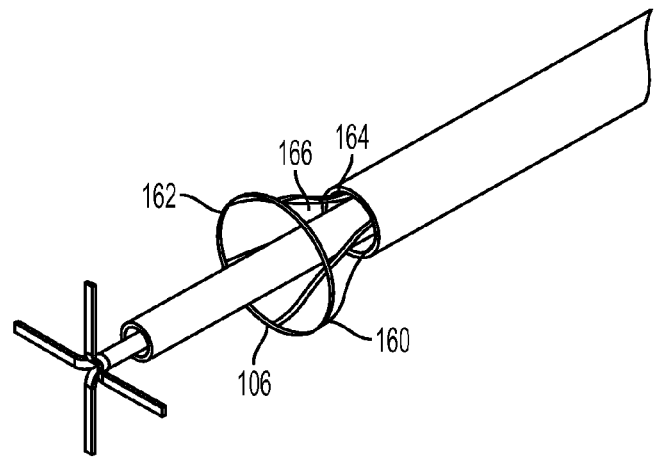
FIG. 10 is a perspective view of an exemplary medical device in accordance with the present teachings.

FIG. 10 illustrates another embodiment of a tissue incising element (160) at its deployed configuration according to the present teachings. In this particular example, the tissue incising element at its expanded profile (160) includes a general continuous cutting edge (106) at a distal end (162), a proximal end (164), an end elongated body (8) (not shown) joining the distal end and the proximal end, and a luminal surface (166). The distal end (162) of the tissue incising element (160) has a generally larger diameter than the proximal end (164). The luminal surface (166) connecting the proximal and distal ends (162, 164) are not continuous, but has a web like surface configuration. Examples of such a web like surface configuration include a coil, a helical spiral, a woven, individual rings, sequential rings with regular connection, periodic connections, a peak-peak connection, a peak-valley connection, and an open cell. Other examples of such a web like surface configuration can be found commonly in the stent design. One ordinarily skilled in the art would understand what has been shown in FIG. 10 is only an example and should not be viewed as limiting to the scope of the present teachings. According to some embodiments, such a web like surface configuration allows the tissue incising element (160) to have a compact delivery profile with a small diameter. Upon being released from a delivery system, the tissue incising element (160) expands either through an elastic recovery process or through a thermal shape memory transition process.

Choosing a method of making a tissue incising element depends mainly on the raw material. In some embodiments, wires are formed into a tissue incising element (160) in various ways by selecting from conventional wire forming techniques, including coiling, braiding, or knitting. In certain embodiments, subsequent welding at specific locations produces a closed-cell wire tissue incising element (160) with an increased longitudinal stability. In other embodiments, a tissue incising element (160) is produced by laser cutting or photochemical etching of a tubing. Similar to what has been described in connection with FIGS. 7-9, the tissue incising element (160) can have a preformed large or small diameter profile and/or can transition from a delivery configuration to a deployed configuration by an elastic recovery, a thermal transformation, or a mechanism enlargement.

Figure 11:
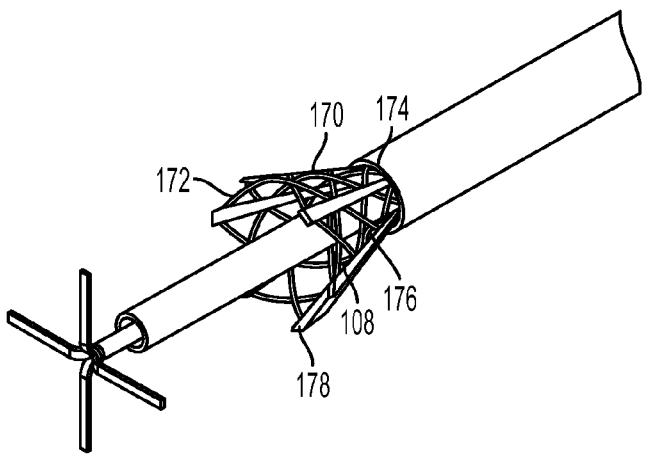
FIG. 11 is a perspective view of an exemplary medical device in accordance with the present teachings.

FIG. 11 illustrates another exemplary tissue incising element (170) at its deployed configuration. Similar to what has been discussed in connection with FIG. 10, the tissue incising element (170) at its expanded profile has a distal end (172), a proximal end (174), and a luminal surface (176) with web-like surface extending between the distal and proximal end. In this particular example, the distal end has a larger dimension than the proximal end. Like the embodiment discussed in connection with FIG. 10, such a web like surface configuration allows the tissue incising element (170) to have a compact delivery profile and expand to a larger deployed profile by an elastic recovery process and a thermal shape memory transition process upon the tissue incising element being released from the delivery system.

In this particular example, the distal end (172) does not include a continuous distal edge. As shown in FIG. 11, the tissue incising element (170) includes a plurality of struts (178) extending from the proximal end (174) to the distal end (172). The struts each has a relative sharp distal tip for engaging the tissue and a sharp cutting edge (108) along one side that faces the adjacent strut. In various embodiments, the tissue incising element (170) is advanced distally outside of the sheath and expands to its deployed profile; the tissue incising element (170) at its deployed profile is further advanced distally so that the distal tips of the struts pierce the target tissue; and the tissue incising element (170) are rotated as indicated by the arrow B, allowing the cutting edge (108) further slicing the tissue. The cross-section of each of the distal portion of the struts can be of any shape as long as it is suitable for tissue incising. Similar to what has been described in connection with FIGS. 7-10, the tissue incising element (170) can have a preformed large or small diameter profile and/or transition from a delivery configuration to a deployed configuration by an elastic recovery, a thermal transformation, or a mechanism enlargement.

Figures 12A, 12B:
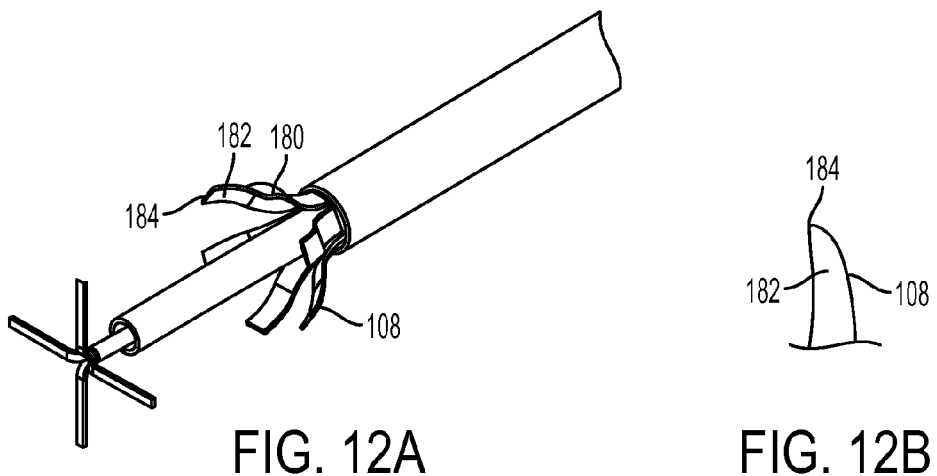
FIGS. 12A-12B are perspective views of an exemplary medical device in accordance with the present teachings.

FIG. 12A illustrates another exemplary tissue incising element (180). In this particular example, the tissue incising element includes a plurality of cutting blades (182) arranged in a circle. In various embodiments, the cutting blades (182) are configured to pivot radially transitioning from a delivery profile to a deployed profile. In its delivery profile, constrained by a sheath, the cutting blades (182) of the tissue incising element (180) pivot inward radially with the distal ends (184) gathered closely and all blades (182) gathered next to one another to form a generally elongated profile. FIG. 12A illustrates a deployed profile of the tissue incising element (180). As shown in FIG. 12A, the tissue incising element extends outside of the distal end of the sheath and all the cutting blades (182) radially pivot outward with the distal ends (184) of the cutting blades (182) extending radially away from the central axis. Similar to what has been described in connection with FIG. 11, the cutting blade (182) can have a sharp distal tip for initially engaging the tissue and a cutting edge (108) along one side that faces an adjacent blade (182), as illustrated in FIG. 12B. Tissue is removed by first piecing the tissue with the distal tip of the cutting blades (182) and rotating the tissue incising element (180) to allow the cutting edges (108) of the blade (182) to incise the tissue. Similar to what has been described herein, the transition from a delivery profile to a deployed profile can be due to an elastic recovery or a thermal-shape transformation.

Now referring to FIGS. 13A-13E, certain exemplary cutting edges (106) of a tissue incising element of the present teachings are provided. According to some embodiments, the distal end of the tissue incising element includes a generally continuous cutting edge (106) along the circumference. In some embodiments, the tissue incising element has a luminal wall with an outer luminal surface (102) and an inner luminal surface (104). As illustrated in FIGS. 13A-13B, the cutting edge (106) includes a single edged bevel. FIG. 13A illustrates cutting edges (106) formed by a single edged bevel tapering from the outer luminal surface (102) to the inner luminal surface (104) and FIG. 13B illustrates a single edged bevel tapering from the inner (104) to the outer luminal surface (102). FIG. 13C shows a cutting edge (106) formed by a double edged bevel tapering from both the outer luminal surface and inner luminal surface (102, 104). Both the embodiments have a general "V" shaped cutting edge and can be used as cutting tools. The angle "θ" of the V shape at the cutting edge can range from 12 to 50 degrees.

In some embodiments, the bevel described herein is formed by removing a portion of the luminal wall by using a proper method, including grinding. According to some embodiments, the edge is formed by a straight bevel as illustrated in FIGS. 13A-13C. In other embodiments, the edge is formed by a conical, cannel, or rolled bevel curves or rolls as shown in FIG. 13D. In yet other embodiments, the edge is formed by a concave grind bevel as illustrated in FIG. 13E. One reasonably skilled in the art could use other designs create a cutting edge in of the tissue incising element without any undue experimentation. Thus what's described and illustrated herein should not be viewed as limiting.

In some embodiments, the mechanical cutting action of the tissue incising element may be coupled with a radio frequency energy source. For example, the radio frequency energy source can be used to thermally ablate tissue in contact with the tissue incising element. Without intending to limit the scope of the present teachings, the ablation action is used to reduce the force required to advance the tissue incisor through the septal wall.

According to some embodiments, the cutting edge (108) of a tissue incising element discussed in connection with FIGS. 11-12 include a single edged bevel, a double edged bevel with the angle "θ" of the cutting edge ranging from 12 to 50 degrees, a straight or curved bevel similar to those described in FIGS. 13A-13E.

In various embodiments, the elongated body (8) and the tissue incising element are parts of an uniform and monolithic body. In such embodiments, the entire elongated body (8) and the tissue incising element is made of one material strong enough for the tissue cutting and flexible enough to be delivered percutaneously into the body. In some embodiments, the tissue incising element is a separate component and is attached to the distal end of the elongated body (8). In such embodiments, the elongated body (8) is made of a flexible material such as polyether-block co-polyamide polymers, for example Pebax™; polyethylene, polytetrafluoroethylene (EPTFE), Fluorinatedethylenepropylene (FEP), polyurethane etc. In addition, in such embodiments, the tissue incising element is made of a hard material such as stainless steel, titanium, ceramic, alloy metal etc. The attachment of the incising element and the elongated body can be achieved by a variety of means, including a mechanical means, for example an interference connection or a threaded connection between the distal portion and the tubular body: an energy means such as heat, laser, ultrasonic, or other types of welding etc; or a chemical means such as adhesive bonding, etc. Other methods of attachment known to those skilled in the art can also be incorporated.

Each of the exemplary tissue stabilizer described in FIGS. 1-6 and each of the tissue incising element described in FIGS. 1-12 can be combined to into a transseptal tissue coring device within the scope of the present teachings.

In some embodiments, the aperture created by a transseptal tissue coring device of the present teachings allows fluid communication between the left and right atria, thereby releasing the left heart pressure. In many embodiments, in order to provide a continuous relief to the left atrium, it is preferred that the aperture between the right and left atria does not re-close itself during a healing process. In certain embodiments, a tissue incising element of the present teachings has a cutting edge with a minimum diameter so that the aperture produced by the incising element also has a minimum size. For example, the cutting edge of the tissue incising element can have a general diameter of 4 mm to 12 mm.

Another aspect of the present teachings relate to methods of delivering and deploying a transseptal coring device. One ordinarily skilled in the art would understand that what is described below are only exemplary methods of percutaneously delivering a transseptal tissue coring device of the present teachings and that other methods can also be used without departing from the spirit of the present teachings. Accordingly, the disclosure should not be viewed as limiting. For example, a transseptal tissue coring device can be delivered without a delivery sheath or a tissue stabilizer can penetrate the septal tissue at its distal end, instead of tracking over a guide wire affixed in the septum beforehand.

Additionally, one ordinarily skilled in the art would also understand that although methods and processes of delivering and/or deploying a transseptal tissue coring device is described with reference to the exemplary devices described in FIGS. 2-3, these methods and/or processes can also be used with other embodiments, including those described in FIGS. 1-12. Thus what is disclosed here should not be viewed as limiting.

According to some embodiments, a transseptal tissue coring device of the present teachings is delivered through a standard right heart catheterization procedure. In such a procedure, the device is delivered through an insertion site on the femoral vein through the inferior vena cava to the right atrium. In some embodiments, a delivery sheath is used to transport a transseptal tissue coring device to a treatment location. In some embodiments, a guide wire is also used to locate a treatment site and assist the delivery of a transseptal tissue coring device to the treatment site.

Figure 14A:
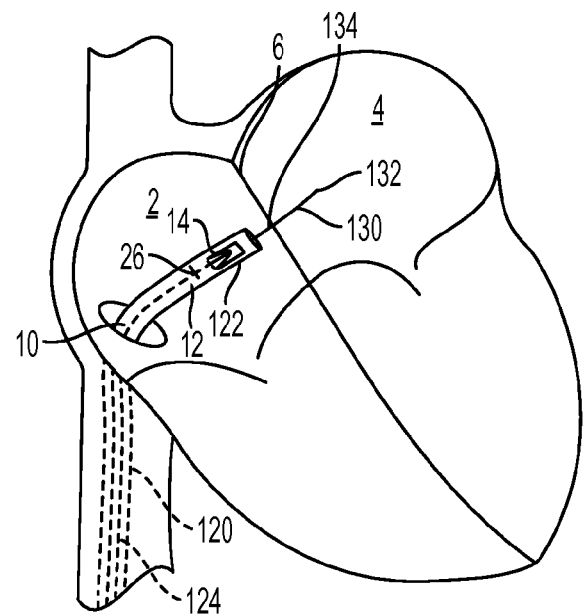
FIGS. 14A-14D are perspective views demonstrating an exemplary process for deploying a medical device in accordance with the present teachings.

Referring to FIG. 14A, according to various embodiments, a transseptal tissue coring device (10) is delivered via a delivery system. In some embodiments, a delivery system includes a delivery sheath (30) with a proximal end (not shown), a distal end (31), a longitudinal lumen (22) extending between the proximal and distal ends and a control mechanism attached to the proximal end of the delivery sheath (30) and configured to control the movement of both the delivery sheath and the transseptal tissue coring device (10). The transseptal tissue coring device (10) in its delivery profile, for example, as illustrated in FIG. 2, is slidably disposed within the central lumen (22) of the delivery sheath (30).

Still referring to FIG. 14A, the delivery system further includes a guide wire (130) to ensure that the transseptal tissue coring device (10) is placed at the desired treatment location. As shown in FIG. 14A, the guide wire (130) has a proximal end (not shown), a distal end (132), and an elongated body (134) extending between the proximal end and the distal end. The proximal end of the guide wire (130) is operably connected to the control mechanism outside of the body. In one embodiment, the guide wire (130) is slidably disposed within the tissue incising element (12) of the transseptal tissue coring device and side by side to the tissue stabilizer (14) of the transseptal tissue coring device (10). In another embodiment, the guide wire is disposed within a central lumen of the tissue stabilizer of the transseptal tissue coring device, for example, the central lumen (74) of the tissue stabilizer (54).

In yet another embodiment of the present teachings, as shown in FIG. 14A, the guide wire (130) is first delivered to the treatment site via a right heart catheterization and pierces through the atrial septum (7) so that the distal end (132) of the guide wire (130) is inside the left atrium (4), as illustrated in FIG. 14A. In some embodiments, a delivery sheath (30) holding a transseptal tissue coring device (12) in its delivery profile inside its central lumen (26) traces over the guide wire (130) and reaches the treatment site. In another embodiment, the transseptal tissue coring device (10) in its elongated delivery profile rides over the guide wire (130) without using a delivery sheath and reaches the treatment location.

Figure 14B:
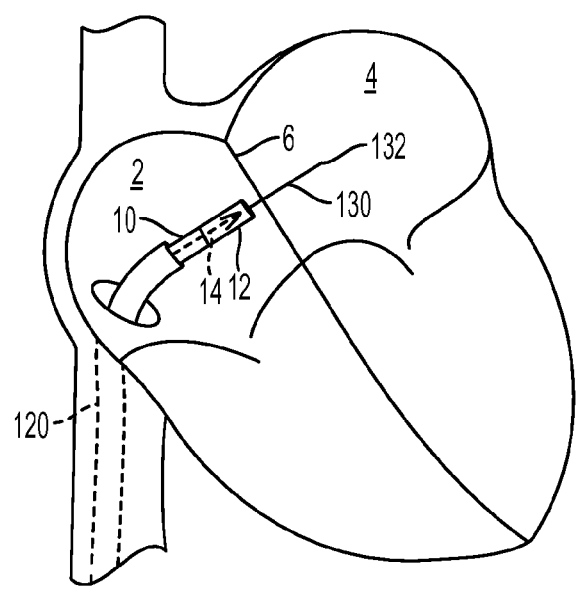

Now referring to FIG. 14B, in some embodiments, the transseptal tissue coring device (10) is deployed by first advancing the coring device distally while holding the delivery sheath (30) held steady so that the tissue incising element (12) holding the tissue stabilizer (14) extends distally beyond the delivery sheath (30) and stops at a location approximate to the atrial septum (7). Alternatively, the delivery sheathing (30) holding the transseptal tissue coring device (10) in its delivery profile is advanced to a location approximate to the atrial septum (7) followed by withdrawing the delivery sheath (30) proximally while the transseptal tissue coring device (10) is held steady.

Figure 14C:
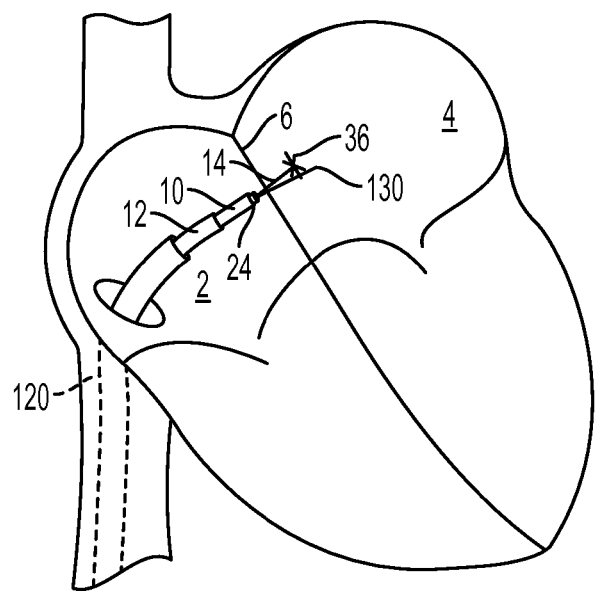
Figure 14D:
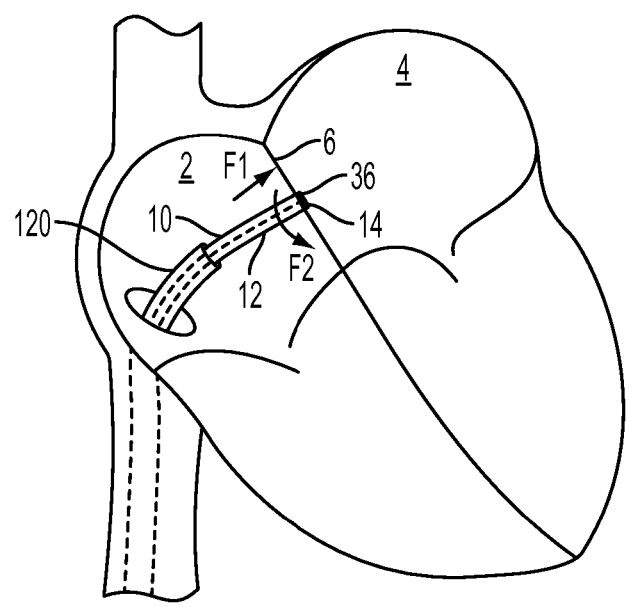

FIG. 14C illustrates an exemplary tissue stabilizer (14) with its distal portion and the tissue supporting struts (36) deployed inside the left atrium (4). In one embodiment, while holding the tissue incising element (12) steady, the tissue stabilizer (14) is advanced distally across the atrial septum (7). This step is achieved by the tissue stabilizer (14) tracing over the guide wire (130) or by the tissue stabilizer (14) piercing through the atrial septum (6) first at its distal end. As the distal portion of the tissue stabilizer (14) extends distally beyond the distal end of the tissue incising element (12), the tissue supporting struts (36) become free from the constraint of the tissue incising element (12) and extend radially outward to form a substantially planar tissue supporting surface. Thus, in certain instances, it is important to manage the distance between the distal end (24) of the tissue incising element (12) to the atrial septum (7), such that the tissue supporting struts (36) do not fully exit from the constraint of the tissue incising element (12) until they are fully inside the left atrium (4). In another embodiment, after the distal portion of the entire transseptal tissue coring device (10) in its delivery profile extends into the left atrium (4), while holding the tissue stabilizer (14), the tissue incising element (12) is retracted proximally to expose the tissue supporting struts (36). In this instance, the tissue supporting struts expand radially inside the left atrium (4) to form a substantially planar tissue supporting surface. In yet another embodiment, a separate sheath holding a tissue stabilizer (14) is used. In this instance, the separate sheath is extended from the right atrium across the atrial septum to the lift atrium, the tissue stabilizer is distally extended outside the separate sheath and the tissue supporting struts expanded radially.

In various embodiments, the deployment of a tissue incising element depends on the deployment of a tissue stabilizer. In various embodiments, the deployment of a tissue incising element is independent from the deployment of a tissue stabilizer. In some embodiments, a tissue incising element is deployed simultaneously as a tissue stabilizer. In some embodiments, a tissue incising element is deployed after the deployment of a tissue stabilizer.

In various embodiments, where a guide wire (130) is not used during a device delivery, a separate transseptal puncture needle can be used to create a small incision on the septum for a tissue stabilizer to cross over. In such embodiments, the tissue stabilizer can slide over the transseptal puncture needle. In other embodiments, the distal end of the tissue stabilizer can be used to perforate the atrial septum and allow the rest of the distal portion of the tissue stabilizer to cross the atrial septum. One reasonably skilled in the art would understand that other devices and/or methods can also be used deliver a tissue stabilizer across the atrial septum. For example, a radio frequency energy source can be coupled to a tissue stabilizer such that the distal end of the tissue stabilizer can create a small hole to allow the distal portion of the tissue stabilizer to cross over the atrial septum.

FIG. 14D illustrates an exemplary tissue coring process with a transseptal tissue coring device (10) according to the present teachings. First, the clinician withdraws the tissue stabilizer (14) proximally so that the radially expanded tissue supporting struts (36) are positioned against the atrial septum from the left atrium. Then the clinician incises tissue from the atrial septum by positioning the tissue incising element (12) against the atrial septum from the right atrium and advancing the tissue incising element (12) distally while holding the tissue stabilizer (14) steady. The tissue is cut by either a direct force "F1", a torque "F2" as illustrated in FIG. 14D, or a combination of both.

Figure 14E:
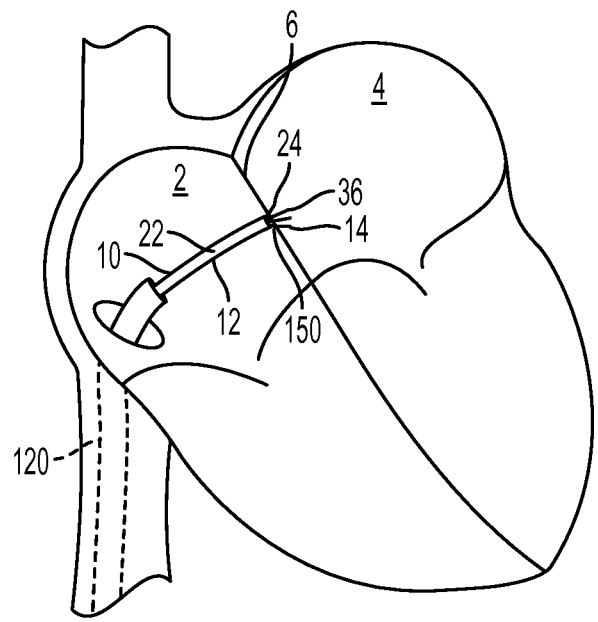
FIGS. 14E-14F are perspective views demonstrating an exemplary process for retrieving a piece of tissue and a medical device in accordance with the present teachings.

FIG. 14E illustrates an exemplary process where a tissue stabilizer (14) captures and removes a piece of the septal tissue (150) from the body. In some embodiments, after septal tissue (150) is incised, the clinical retracts the tissue stabilizer (14) proximally inside the tissue incising element (12) and the tissue stabilizer carries the removed tissue (150). Specifically, as illustrated in FIG. 14E, as the tissue stabilizer (14) retracts proximally back into the tissue incising element (12), the distal end (24) of the tissue incising element (12) pushes the detached septal tissue (150) against the tissue supporting struts (36), and the tissue (150) and the tissue supporting struts (36) fold inward distally and enter the distal end (24) of the tissue incising element (12). The detached tissue (150) is captured between the folded tissue supporting struts (36) and the inner luminal wall of the tissue incising element (12).

Figure 14F:
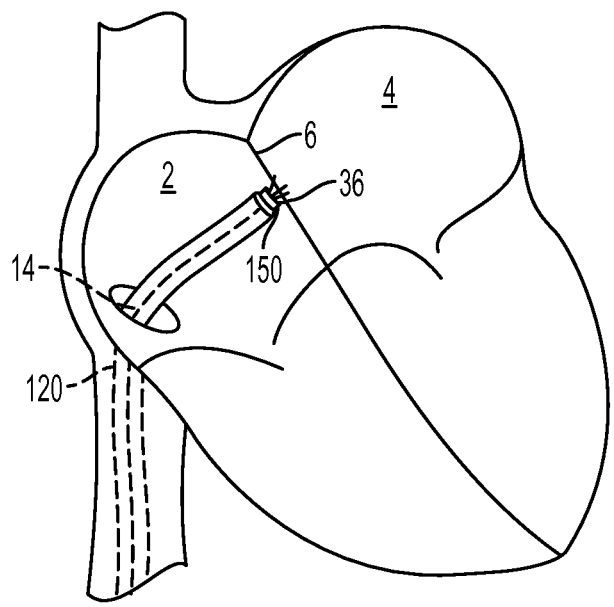

In an alternative embodiment, as illustrated in FIG. 14F, after the tissue is incised, the tissue incising element (12) is retracted proximally and removed from the body while the delivery sheath (30) is advanced distally to a proximity of the atrial septum (7). Then, the tissue supporting struts (36) along with the detached septal tissue (150) are folded distally inward and enter the sheath from its distal end. The entire system including the sheath and the tissue stabilizer is then removed from the body as illustrated in FIG. 14F.

On reasonably skilled in the art would understand that a control mechanism can be used to manage the motion of the delivery sheath, the tissue incising element, the tissue stabilizer, and the guide wire, each of which is described herein. In some embodiments, each of the delivery sheath, the tissue incising element, the tissue stabilizer, and the guide wire moves independently. In other embodiments, motions of the delivery sheath, the incising element, the tissue stabilizer, and the guide wire can be linked to one another for convenience.

The present teachings are capable of other embodiments or of being practiced or carried out in various other ways. Also, it is to be understood that the phraseology and terminology employed herein is for the purpose of description and should not be regarded as limiting.

Unless otherwise defined, all technical and scientific terms used herein have the same meaning as commonly understood by one of ordinary skill in the art to which these present teachings belong. Methods and materials similar or equivalent to those described herein can be used in the practice or testing of the present teachings. In case of conflict, the patent specification, including definitions, will control. In addition, the materials, methods, and examples are illustrative only and not intended to be limiting.

We claim:

1. A transseptal tissue coring device comprising a cutting edge and a supporting surface, each of which comprises a delivery profile and a deployed profile;
   wherein at least one dimension of the cutting edge in the deployed profile is up to 400% of that in the delivery profile; and
   the cutting edge in the deployed profile is capable of applying a force against the supporting surface in the deployed profile to cut tissues; and
   the supporting surface is derived from a tubular body having a proximal end, a distal end, and a plurality of slits extending substantially from the proximal end to the distal end;
   wherein the deployed supporting surface is substantially parallel to a surface formed by the deployed cutting edge and is greater than the dimension of the deployed cutting edge.

2. The transseptal tissue coring device of claim 1, wherein the at least one dimension of the cutting edge in the deployed profile is about 4 mm.

3. The transseptal tissue coring device of claim 1, wherein at least one dimension of the cutting edge in the delivery profile is greater than that of the supporting surface in the delivery profile.

4. The transseptal tissue coring device of claim 1, wherein the cutting edge comprises a plurality of flaps.

5. The transseptal tissue coring device of claim 1, wherein the supporting surface comprises one or more supporting struts.

6. The transseptal tissue coring device of claim 1, wherein each of the slits is parallel to the longitudinal axis of the tubular body.

7. The transseptal tissue coring device of claim 1, wherein each the slits is spiral along the tubular body.

8. The transseptal tissue coring device of claim 1, wherein the device is configured to percutaneously remove internal tissue.

9. The transseptal tissue coring device of claim 8, wherein the internal tissue is from the atrial septum.

10. A transseptal tissue coring device comprising:
    a tissue incising element comprising a proximal end, a distal end, a longitudinal lumen extending from the proximal end to the distal end, and a sharp edge at the distal end, and
    a tissue stabilizer comprising an elongated body, a distal portion, and a plurality of tissue supporting struts formed by a plurality of slits along the elongated body of the distal portion of the tissue stabilizer, wherein the tissue supporting struts form a supporting surface, wherein the supporting surface is substantially parallel to a surface formed by the sharp edge of the tissue incising element; and
    is greater than the dimension of the sharp edge of the tissue incising element.

11. The transseptal tissue coring device of claim 10, wherein each of the tissue supporting struts comprises a fixed end attaching to the elongated body and a free end extending radially away from the elongated body of the tissue stabilizer.

12. The transseptal tissue coring device of claim 10, wherein the tissue stabilizer comprises a delivery profile and a deployed profile and the tissue stabilizer is slidably disposed within the longitudinal lumen of the tissue incising element in its delivery profile.

13. The transseptal tissue coring device of claim 12, wherein the tissue supporting struts are stowed radially along the elongated body of the tissue stabilizer in the delivery profile.

14. The transseptal tissue coring device of claim 12, wherein the tissue supporting struts expand radially outward forming the supporting surface in the deployed profile.

15. A method of percutaneously removing tissue from the heart comprising:
    providing a transseptal tissue coring device according to claim 10;
    advancing the transseptal tissue coring device to a proximity of the atrial septum, expanding the tissue supporting struts of the tissue stabilizer radially and
    positioning the tissue stabilizer against the atrial septum inside the left atrium,
    positioning the tissue incising element against the atrial septum inside the right atrium,
    advancing the tissue incising element distally,
    incising tissue from the atrial septum, and
    capturing the removed septal tissue inside the transseptal tissue coring device.

* * * * *